(12) United States Patent
Nikishov et al.

(10) Patent No.: US 12,295,710 B2
(45) Date of Patent: May 13, 2025

(54) DEVICE AND METHOD FOR HUMAN BODY IMPEDANCE ANALYSIS INSENSITIVE TO HIGH CONTACT IMPEDANCE AND PARASITIC EFFECTS

(71) Applicant: Samsung Electronics Co., Ltd., Suwon-si (KR)

(72) Inventors: Artem Yurievich Nikishov, Moscow (RU); Konstantin Alexandrovich Pavlov, Moscow (RU); Namseok Chang, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 280 days.

(21) Appl. No.: 17/940,655

(22) Filed: Sep. 8, 2022

(65) Prior Publication Data

US 2023/0016653 A1 Jan. 19, 2023

Related U.S. Application Data

(63) Continuation of application No. PCT/KR2022/008590, filed on Jun. 17, 2022.

(30) Foreign Application Priority Data

Jun. 18, 2021 (RU) ................................ 2021117779

(51) Int. Cl.
*A61B 5/053* (2021.01)
*A61B 5/00* (2006.01)
*A61B 5/0537* (2021.01)

(52) U.S. Cl.
CPC ............ *A61B 5/053* (2013.01); *A61B 5/0537* (2013.01); *A61B 5/681* (2013.01); *A61B 5/7225* (2013.01)

(58) Field of Classification Search
CPC ..... A61B 5/053; A61B 5/0531; A61B 5/0537; A61B 5/681; A61B 5/7225; G01R 15/14; G01R 19/0084
See application file for complete search history.

(56) References Cited

U.S. PATENT DOCUMENTS 6,393,317 B1 * 5/2002 Fukuda ................ A61B 5/4869
600/382
6,473,641 B1 * 10/2002 Kodama .............. A61B 5/4869
600/547

(Continued)

FOREIGN PATENT DOCUMENTS

CN    106849711 A    6/2017
CN    105262553 B    7/2017

(Continued)

OTHER PUBLICATIONS

Russian Search Report dated Jan. 14, 2022, issued in Russian Patent Application No. 2021117779.

(Continued)

*Primary Examiner* — Steven L Yeninas
(74) *Attorney, Agent, or Firm* — Jefferson IP Law, LLP

(57) ABSTRACT

A device for bioimpedance determining is provided. The device includes contact electrodes for contacting with one part of the user's body and for contacting with another part of the user's body, an alternating current source, a current measurement circuit, a voltage measurement circuit in the region of one of the contact electrodes for contacting with one part of the user's body, and in the region of one of the contact electrodes for contacting with another part of the user's body, a switch connected to the alternating current (AC) source and to the current measurement circuit and configured to form a first and a second current measurement paths so that the current flows through the user's body from one part of the body to another part of the body, and a control (Continued)

unit configured to determine the user's bioimpedance based on the measured current and voltage values.

20 Claims, 35 Drawing Sheets

(56) References Cited

U.S. PATENT DOCUMENTS

| | | | | |
|---|---|---|---|---|
| 6,532,384 | B1* | 3/2003 | Fukuda | A61B 5/0537 600/587 |
| 10,285,620 | B2 | 5/2019 | Jung et al. | |
| 10,368,773 | B2 | 8/2019 | Jung et al. | |
| 10,555,686 | B1* | 2/2020 | Kimoto | A61B 5/0535 |
| 10,959,641 | B2 | 3/2021 | Jung et al. | |
| 10,993,645 | B2 | 5/2021 | Naseri et al. | |
| 2004/0220538 | A1 | 11/2004 | Panopoulos | |
| 2011/0112428 | A1 | 5/2011 | Hsieh et al. | |
| 2018/0206761 | A1 | 7/2018 | Jung et al. | |
| 2019/0053736 | A1 | 2/2019 | Kwon | |
| 2019/0167144 | A1 | 6/2019 | Jung et al. | |
| 2019/0175055 | A1 | 6/2019 | Eom et al. | |
| 2019/0246942 | A1 | 8/2019 | Moreva et al. | |
| 2020/0060576 | A1 | 2/2020 | Korkala et al. | |
| 2020/0064906 | A1 | 2/2020 | Cha | |
| 2021/0003523 | A1* | 1/2021 | Chandak | G01N 27/028 |
| 2022/0071503 | A1 | 3/2022 | Chang et al. | |

FOREIGN PATENT DOCUMENTS

| | | |
|---|---|---|
| CN | 106999164 A | 8/2017 |
| CN | 102756625 B | 2/2018 |
| CN | 105335564 B | 5/2018 |
| CN | 105426581 B | 9/2018 |
| DE | 2800574 A1 | 7/1979 |
| EP | 3 287 072 A1 | 2/2018 |
| GB | 990296 A | 4/1965 |
| JP | 2015-002779 A | 1/2015 |
| KR | 10-2018-0087043 A | 8/2018 |
| KR | 10-2020-0078955 A | 7/2020 |
| RU | 2664633 C2 | 8/2018 |
| WO | 2020/138667 A1 | 7/2020 |

OTHER PUBLICATIONS

Russian Office Action dated Jan. 14, 2022, issued in Russian Patent Application No. 2021117779.

Russian Decision on Grant dated Apr. 1, 2022, issued in Russian Patent Application No. 2021117779.

International Search Report and Written Opinion dated Oct. 21, 2022, issued in International Patent Application No. PCT/KR2022/008590.

European Search Report dated Aug. 2, 2024, issued in European Application No. 22825369.6.

* cited by examiner

DEVICE AND METHOD FOR HUMAN BODY IMPEDANCE ANALYSIS INSENSITIVE TO HIGH CONTACT IMPEDANCE AND PARASITIC EFFECTS

CROSS-REFERENCE TO RELATED APPLICATION(S)

This application is a continuation application, claiming priority under § 365(c), of an International application No. PCT/KR2022/008590, filed on Jun. 17, 2022, which is based on and claims the benefit of a Russian patent application number 2021117779, filed on Jun. 18, 2021, in the Russian Intellectual Property Office, the disclosure of which is incorporated by reference herein in its entirety.

BACKGROUND

1. Field

The disclosure relates to the field of researching physical properties of biological tissues. More particularly, the disclosure relates to devices and methods for bioimpedance analysis (BIA) of human body composition.

2. Description of Related Art

In professional medicine, bioimpedance analysis (BIA) or bioimpedance measurement is known for a relatively long time and is applied to measure body composition—a non-invasive method that allows analyzing the body composition in a short time to determine amount of fluid, mass of fat and muscle, bone tissue, body mass index, metabolic conversion rate, biological age, predisposition to some or other diseases, etc. However, due to the fact that this required special equipment with relatively large contact electrodes, which required certain costs and a trip to a specialized center having such equipment, the main users of this procedure were athletes, as well as people for whom controlling their body composition was very important, for example, those who have suffered injuries or are obese.

Meanwhile, in recent years, publications have appeared demonstrating that for measuring the human body impedance the usage of large contact electrodes is not necessary, but rather sufficient is to use compact electrodes. Since they can be embedded in electronic devices, this has prompted the embedding of bioimpedance analysis methods into small wearable devices such as smartwatches and fitness bracelets, that is extremely attractive for a wide range of health-conscious, fitness-oriented, weight-loss users, and etc.

However, while smaller electrode sizes are better suited to the form factor of wearable electronics, they tend to degrade BIA accuracy since the body contact area decreases and the contact impedance increases accordingly. Moreover, skin condition in the part of the body that a person touches the contact electrodes has a significant effect on the value of the contact impedance, that is, the range of impedances is also relatively large from lower values for highly moisturized skin to larger values for dry or diseased skin, which is also negatively affects the measurement error. Further, since modern wearable devices have a complex design that contains many different functions and sensors, the same electrodes and buttons are often used for many different purposes, that is, other circuits may be adjacent to the impedance measurement circuit, which can introduce parasitic effects into it, that can lead to additional degradation in the measurement accuracy.

FIG. 1A shows an example of a procedure for measuring body impedance using a modern smartwatch according to the related art, and FIG. 1B depicts an impedance measurement (BIS) structure embedded in such watch according to the related art.

The watch, being fixed on the wrist of one hand, has on its bottom surface two electrodes #2 and #4 being in contact with the wrist, and the other two electrodes #1 and #3 are placed on the side buttons, which the user touches, respectively, with the fingers of the other hand. As can be noted, unlike professional medical equipment, in this arrangement, the electrodes contact directly with the BIS structure. Other elements and integrated circuits (IC) (for example, extra sensors, electrocardiogram meters (ECG), diodes, voltage control, wireless charging, etc.), which become sources of parasitic effects, are connected to the same electrodes. Accordingly, for isolation between the BIS and these parasitic elements, it is also necessary to install additional external elements (S1 . . . S4).

With respect to specific technical solutions in the field of bioimpedance analysis, related to the disclosure to one or another degree, document WO 2020/138667 A1 (02.07.2020), which discloses an electronic device comprising a biological body contact circuit, including four electrodes; a current-voltage measurement module including a power supply port, a current measurement port, a first voltage measurement port, a second voltage measurement port, an alternating current signal generator electrically connected to the power supply port, an ammeter electrically connected to the current measurement port, and a voltmeter interposed between and electrically connected to the first voltage measurement port and the second voltage measurement port; a processor; a memory electrically connected to the processor to store the characteristic impedance values of circuit elements interposed between and electrically connected to the current-voltage measurement module and the biological body contact circuit, and to store values for parasitic impedance stemming from parasitic elements existing between the biological body contact circuit and a ground; and a current-voltage path configuration module configured to electrically connect the biological body contact circuit to the power supply port, the current measurement port, the first voltage measurement port, and the second voltage measurement port such that the voltage path and current path of the biological body contact circuit can be changed under control of the processor. Such solution is suitable for implementation as part of a wristwatch. However, since this document proposes to consider external (relative to the BIS circuit itself) parasitic and circuit elements, it is necessary to know the final embodiment of the entire device in advance in order to enter data about these elements into the memory. The very fact of using the memory is also undesirable, since in such a compact device important is to minimize any memory consumption. In addition, the circuit proposed in this document is very sensitive to the high contact impedance of the skin (operates incorrectly in such situations), and the size of the electrodes cannot be reduced.

U.S. Pat. No. 10,285,620 B2 (14.05.2019) discloses a method of measuring a bio signal using a bio signal measuring apparatus, including positioning electrodes included as part of the bio signal measuring apparatus to contact a surface of an examinee; switching an impedance measurer included as part of the bio signal measuring apparatus and including a voltmeter and a current source; measuring a first impedance value of the examinee while operating the impedance measurer according to a first mode; switching the impedance measurer to a second mode; measuring a second impedance value of the examinee while operating the impedance measurer according to a second mode; and obtaining bio impedance of the examinee based on the first and second impedance values and an internal impedance of the current source. As in the previous solution, the circuit proposed in this document is very sensitive to the high contact impedance of the skin, and the size of the electrodes cannot be reduced. Moreover, unlike the previous solution, external parasitic and circuit elements are not considered here, which, together with other disadvantages, makes it impossible to implement this method as part of a wristwatch.

US 2020/064906 A1 (27.02.2020) discloses a wearable terminal with a terminal main body and a band connected to the terminal main body so as to be wearable on a body part including a wrist. The terminal may include a detection circuit, a first electrode and a second electrode which are connected to the detection circuit, and a control unit for controlling the wearable terminal to perform a pre-configured function when a part of a user's body comes into contact with the first electrode and the second electrode simultaneously, and the detection circuit, the first electrode, and the second electrode then form a signal pathway through the user's body. This solution, in fact, describes only an abstract measurement method, while the schematic features of the detection circuit are not disclosed. In addition, based on knowledge of the rest of the state of the art, it can be assumed that this solution will also require knowledge of parasitic elements, and the circuit will also be sensitive to high contact impedance of the skin.

US 2019/246942 A1 (15.08.2019) discloses a wearable device configured to perform a plurality of functions including a first function to measure a body composition parameter of a user wearing the device and one or more second functions requiring an input from the user. The device comprises a first electrode on an inner surface of the device arranged, when the device is worn by a user, to contact the body of the user; a second electrode on an outer surface of the device arranged to be touched by the user; a touch controller arranged to detect when a user touches the second electrode; a body composition parameter measurement device arranged, when the user is in contact with the second electrode, to measure a body impedance of the user by passing a current between the first and second electrodes and detecting a voltage generated between the first and second electrode in response to the current, and to use the measured body impedance to determine a value of a body composition parameter. In this solution, the finger impedance is included in the measurement, resulting in an inaccurate BIA estimate. As with previous solutions, this solution will also require knowledge of parasitic elements, and the circuit will also be sensitive to the high contact impedance of the skin.

Summarizing the known solutions, the equivalent bioimpedance measurement circuits shown in FIGS. 2A to 2C can be obtained.

FIGS. 2A, 2B, and 2C show generalized equivalent bioimpedance measurement circuits according to the related art.

Referring to FIGS. 2A, 2B, and 2C, when the watch is fixed on the wrist of one (for example, left) hand of the user, and with the fingers of the other (for example, right) hand, the user touches the contact electrodes (for example, placed on the side buttons), as shown in FIG. 2A, then current flows between electrodes #1, #3 and #2, #4, while the human body has an impedance in the path of current flow between these electrodes. A corresponding equivalent human body model is depicted within box A in FIG. 2B. The measurements are performed by the BIA circuit, which is shown in box C.

However, as mentioned above, a modern wearable device can have many other adjacent elements in addition to the BIA circuit—respectively, external and parasitic elements are shown in box B.

In turn, block A can be represented in the form of a more detailed equivalent circuit of the human body (see FIG. 2C), wherein there is a corresponding contact impedance $Z_{c1}$ ... $Z_{c4}$ between each of the electrodes #1 ... #4 and the impedance $Z_b$. All parasitic effects and external elements can be combined in the block B equivalent circuit as parallel parasitic impedances $Z_{p1}$ ... $Z_{p4}$ and serial parasitic impedances $Z_{s1}$ ... $Z_{s4}$ connected to each electrode.

Contact impedances in humans can reach very high values (up to 50 k$\Omega$ for contact electrodes touching fingers), that leads to a large error in determining the body impedance. Accordingly, in order to avoid large errors, an accurate determination of the values of the elements of block B is required, however, they are difficult to be accurately and unambiguously determined in order to create a universal measurement method that takes into account parasitic effects for different devices, since modern compact wearable devices have a complex structure, are produced in a wide variety of models with a different set of functions, different component base, different topologies of printed circuit boards, different positions and sizes of electrodes, different types of materials, etc., that is, they change from device to device. Thus, even if one database is created for plurality of users for one model, then it will no longer be possible to be used for other models and for other methods.

FIG. 3 is a graph comparing bioimpedance measurement errors for multiple users according to the related art.

Referring to FIG. 3, to demonstrate that contact impedances, parasitic effects and external elements shall be taken into account in the prior art solutions, FIG. 3 shows a graph comparing bioimpedance measurement errors for multiple users (more than 2500), which shows how the accuracy of calculating body impedance is degraded in one of the above prior art devices in case 1, when block B is not taken into account (blue line) compared to case 2 when block B is taken into account (red line). In case 1, all errors are almost the same for all users—about 15%, which is acceptable accuracy for a compact wearable device. In case 2, the error in determining the body impedance becomes very high for users with high contact impedance, reaching 250-300% for some users.

Thus, in the related art, a need has arisen to create a device and a method for BIA, which would eliminate the following disadvantages of existing solutions:
  the need to consider external parasitic and circuit elements;
  usage of additional memory;
  sensitivity to high contact impedance of the skin;
  impossibility of reducing the electrode size;
  impossibility of creating a universal measurement database.

The above information is provided as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a device and a method for bioimpedance analysis (BIA) of human body composition which are insensitive to high contact impedance, external elements and parasitic effects.

Additional aspects will be set forth in part in the description which follows and, in part, will be apparent from the description, or may be learned by practice of the presented embodiments.

In accordance with an aspect of the disclosure, a device for bioimpedance determining is provided. The device includes first and third contact electrodes configured to contact a first part of a user's body, a second and a fourth contact electrodes configured to contact a second part of the user's body, the first part being different from the second part, an alternating current source, a current measurement circuit, wherein the alternating current source and the current measurement circuit have a common ground, at least one voltage measurement circuit configured to measure a voltage between one of the first and third contact electrodes and the common ground, and between one of the second and fourth contact electrodes and the common ground, a first switch including four ports, a first port being connected to the alternating current source, a second port being connected to the current measurement circuit, the first switch having at least two states and configured to form, in a first state and a second state, respectively, a first and a second current measuring paths so that the current flows through the user's body from the first part of the body to the second part of the body, and a control unit connected to the first switch, to the current measurement circuit and to the at least one voltage measurement circuit, and configured to control states of the first switch, receive current and voltage values measured by the current measurement circuit and the at least one voltage measurement circuit for each current measurement path, and determine the user's bioimpedance based on the received current and voltage values.

In one embodiment, the first switch has the first state, in which the first and the second ports are connected, respectively, with the third and the fourth ports, and the second state, in which the first and the second ports are connected, respectively, with the fourth and the third ports.

In one embodiment, the third port of the first switch is electrically connected to the first contact electrode, the fourth port of the first switch is electrically connected to the second contact electrode.

In one embodiment, the voltage measurement circuit is an ammeter with an impedance connected in series or a voltmeter.

In one embodiment, the current measurement circuit is a voltmeter with an impedance connected in parallel or an ammeter.

In one of the embodiments of the first aspect, a number of voltage measurement circuits is two, the first voltage measurement circuit is electrically connected to the third contact electrode and the common ground, and the second voltage measurement circuit is electrically connected to the fourth contact electrode and the common ground.

In one embodiment, the number of voltage measurement circuits is one, and the device further includes a fourth switch configured to alternately connect each of the third and fourth contact electrodes to a voltage measurement circuit for each of the current measurement paths.

In one embodiment, the device further includes a second and a third switches, each of which includes four ports and is connected to the control unit, wherein the third port of the first switch is connected to the third port of the second switch, the fourth port of the first switch is connected to the fourth port of the third switch, the first and the second ports of the second switch are electrically connected, respectively, to the first and the third contact electrodes, the first and the second ports of the third switch are electrically connected, respectively, to the fourth and the second contact electrodes, the fourth port of the second switch and the third port of the third switch are intended to be connected to at least one voltage measurement circuit, wherein the first, the second and the third switches have at least two states and are configured to jointly form at least four different current measurement paths so that the current flows though the user's body from one body part to another body part.

In one embodiment, the number of voltage measurement circuits is two, the first voltage measurement circuit is connected to the fourth port of the second switch and the common ground, and the second voltage measurement circuit is connected to the third port of the third switch and the common ground.

In one embodiment, the number of voltage measurement circuits is one, and the device further includes the fourth switch configured to alternately connect each of the fourth port of the second switch and the third port of the third switch to the voltage measurement circuit for each of the current measurement paths.

In one embodiment of the first aspect, the device further includes at least one additional element and/or a circuit that causes a serial and/or parallel parasitic impedance in the circuit between a corresponding contact electrode and a corresponding switch port, and/or in the circuit between a corresponding contact electrode and a corresponding terminal of the voltage measurement circuit.

In accordance with another aspect of the disclosure, a method for bioimpedance determining performed in a device for determining bioimpedance is provided. The method includes controlling a first switch to change a state of the switch to a first state or a second state for forming, respectively, a first or a second current measurement paths in which the current flows through the user's body through contact electrodes contacting a first part of the user's body to contact electrodes contacting with a second part of the user's body, or in the opposite direction, in each of the current measurement paths, the current ($I_1$, $I_2$) is measured in a region of the contact electrode, to which the current flows through the user's body, in each of the current measurement paths, the voltage ($U_{a1}$, $U_{a2}$) is measured in the region of another contact electrode contacting the first part of the user's body, and the voltage ($U_{b1}$, $U_{b2}$) in the region of another contact electrode, contacting the second part of the user's body, and determining bioimpedance ($Z_b$) of the user based on the measured current and voltage values.

In one embodiment, the user's impedance is determined in accordance with following formula.

$$Z_b = \frac{\frac{U_{a1}}{U_{b1}} - \frac{U_{b1}}{U_{a1}} + \frac{U_{a2}}{U_{b2}} - \frac{U_{b2}}{U_{a2}}}{I_1\left(\frac{1}{U_{a1}} + \frac{1}{U_{b1}}\right) + I_2\left(\frac{1}{U_{a2}} + \frac{1}{U_{b2}}\right)}.$$

In one embodiment, the method further includes determining a corrected bioimpedance ($Z_{bcorr}$) of the user based on the determined bioimpedance ($Z_b$) of the user by using a pretrained neural network.

In one embodiment, the method further includes training a neural network by a method of linear regression, using a model aimed at minimizing an error between the reference bioimpedance ($Z_{bref}$) values, measured for each user from a training sample on a reference equipment, and bioimpedance ($Z_b$) values, determined for each user from the training sample.

In one embodiment, the training model further considers at least one of the following parameters for each user from the training sample weight, height, age, gender, race, waist circumference, hip circumference, wrist circumference.

In one of the embodiments of the second aspect, the device for bioimpedance determining further includes controlling states of first switch, a second switch, and a third switch to form four different current measurement paths, in which the current flows through the user's body through one of the contact electrodes contacting the first part of the user's body, to one of the contact electrodes contacting the second part of the user's body, in each of the current measurement paths, a current ($I_1$, $I_2$, $I_3$, $I_4$) is measured in the region of said one contact electrode to which the current flows through the user's body, in each of the current measurement paths, the voltage ($U_{a1}$, $U_{a2}$, $U_{a3}$, $U_{a4}$) is measured between the contact electrodes contacting the first part of the user's body and the ground, and the voltage ($U_{b1}$, $U_{b2}$, $U_{b3}$, $U_{b4}$) between the contact electrodes contacting the second part of the user's body and the ground, and determining the bioimpedance ($Z_b$) of the user based on the measured values of current and voltage in accordance with following formula.

$$Z_b = \frac{\frac{U_{a1}}{U_{b1}} - \frac{U_{b1}}{U_{a1}} + \frac{U_{a2}}{U_{b2}} - \frac{U_{b2}}{U_{a2}} + \frac{U_{a3}}{U_{b3}} - \frac{U_{b3}}{U_{a3}} + \frac{U_{a4}}{U_{b4}} - \frac{U_{b4}}{U_{a4}}}{I_1\left(\frac{1}{U_{a1}} + \frac{1}{U_{b1}}\right) + I_2\left(\frac{1}{U_{a2}} + \frac{1}{U_{b2}}\right) + I_3\left(\frac{1}{U_{a3}} + \frac{1}{U_{b3}}\right) + I_4\left(\frac{1}{U_{a4}} + \frac{1}{U_{b4}}\right)}.$$

The disclosure provides BIA devices and methods that provide improving accuracy of bioimpedance determining up to values comparable to professional devices, without the need to consider contact impedances, external components, and parasitic effects.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the disclosure defined by the claims and their equivalents. It includes various specific details to assist in that understanding, but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but are merely used by the inventor to enable a clear and consistent understanding of the disclosure. Accordingly, it should be apparent to those skilled in the art that the following description of various embodiments of the disclosure is provided for illustration purposes only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1A:
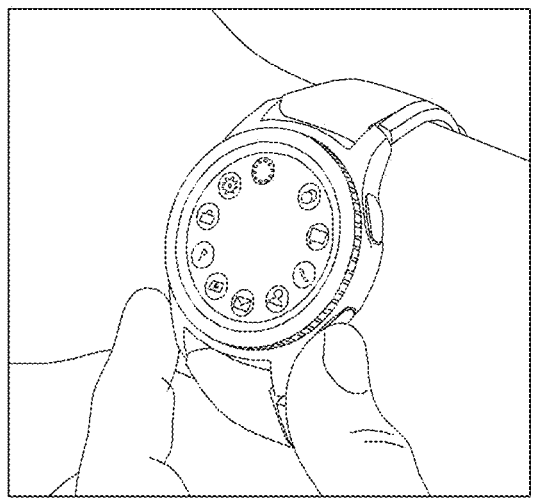
FIG. 1A shows an example of a body impedance measurement procedure using a modern smartwatch from the user's point of view according to the related art.
Figure 1B:
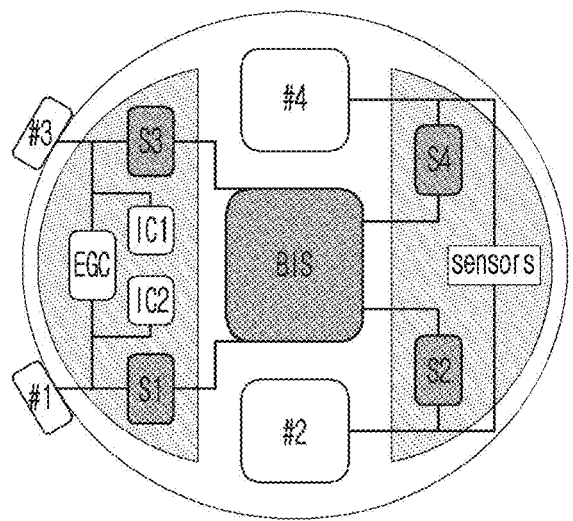
FIG. 1B depicts an impedance measurement (BIS) structure embedded in the watch of FIG. 1A according to the related art.
Figure 2A:
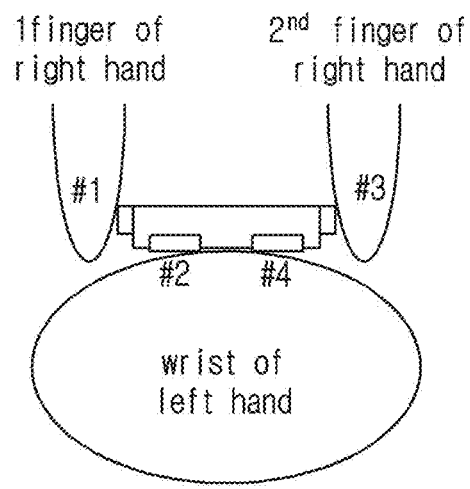
FIGS. 2A, 2B, and 2C show generalized equivalent bioimpedance measurement circuits according to the related art.
Figure 2B:
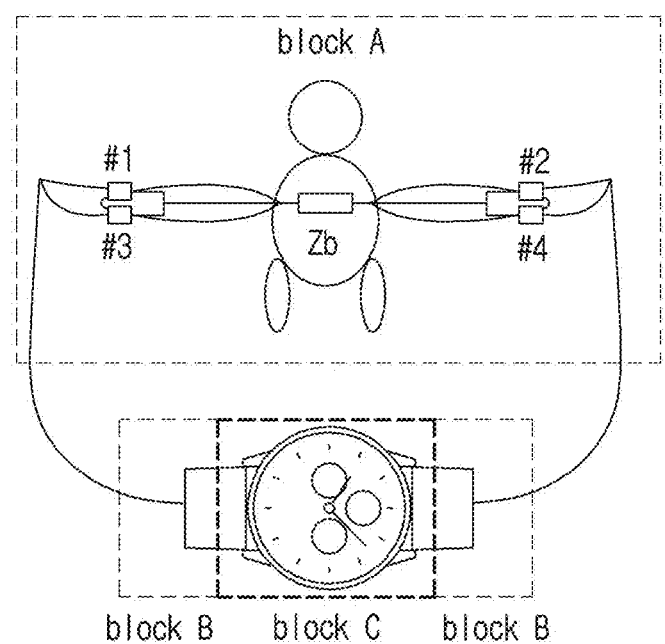
Figure 2C:
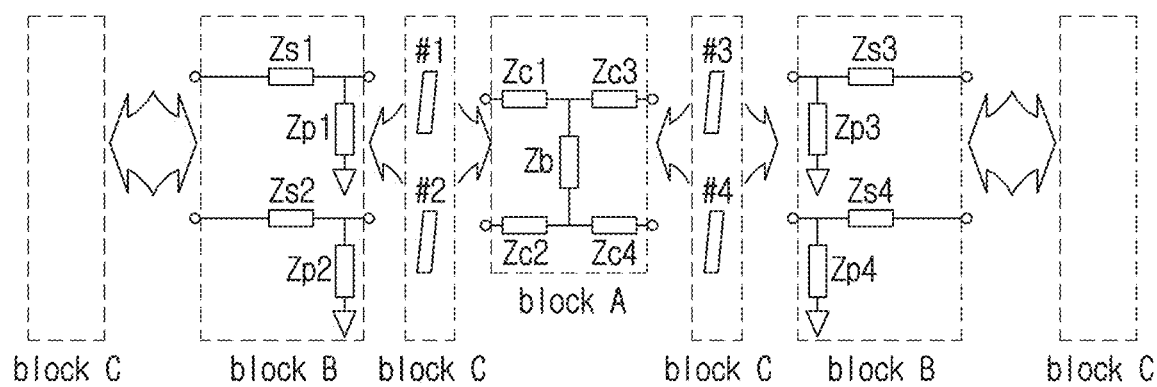
Figure 3:
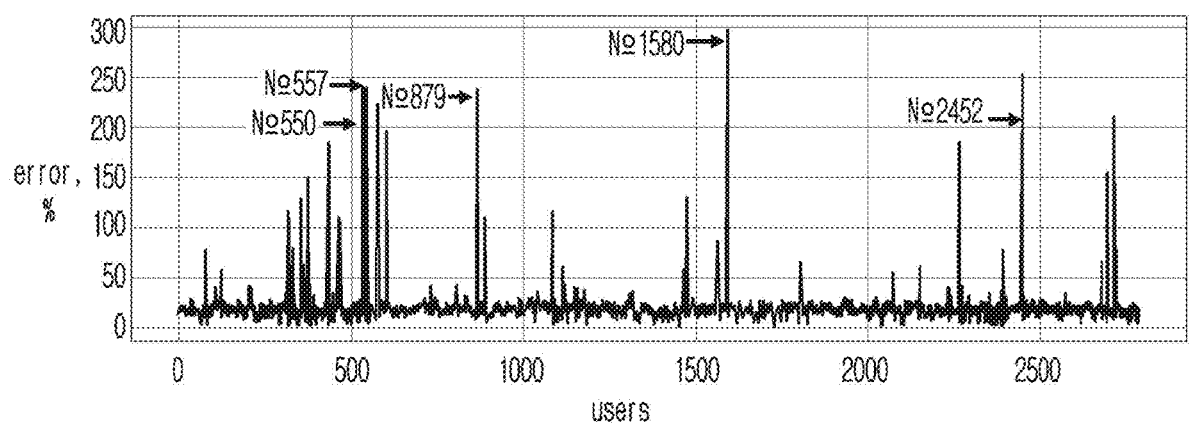
FIG. 3 is a graph comparing bioimpedance measurement errors for multiple users according to the related art.
Figure 4:
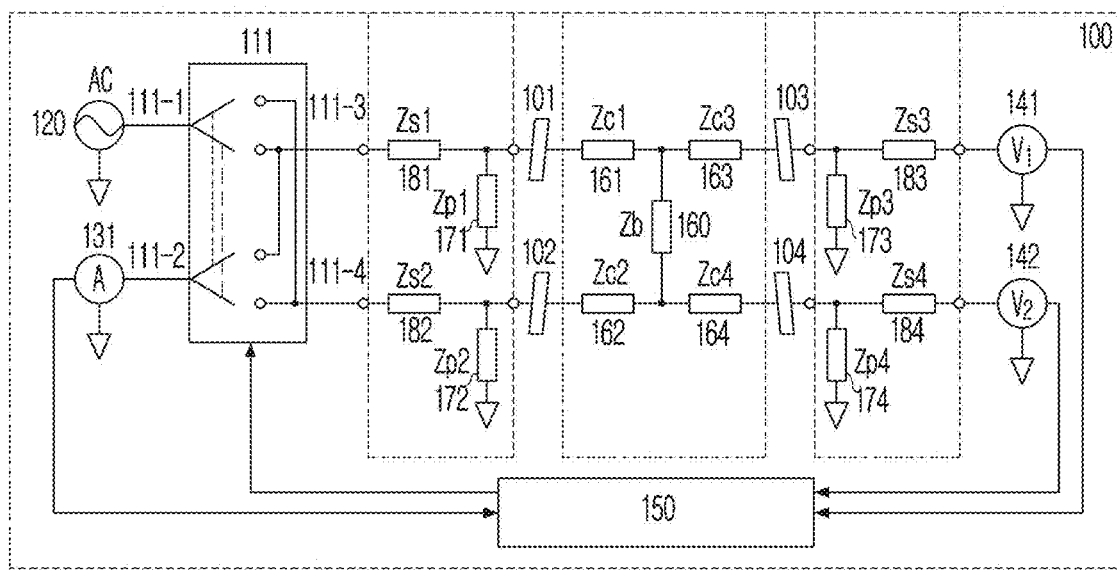
FIG. 4 is an equivalent circuit diagram of the device for determining a human body impedance according to an embodiment of the disclosure.

FIG. 4 shows an equivalent circuit diagram of a device 100 for determining a human body impedance according to an embodiment of the disclosure.

Referring to FIG. 4, the device 100 comprises contact electrodes 101, 102, 103, and 104, two of which are intended for contact with one part of the user's body (e.g., electrodes 102 and 104 for contact with the wrist of one hand), and the other two are intended for contact with another part of the user's body (e.g., electrodes 101 and 103—for contact with the tips of two fingers of the other hand).

The device 100 further comprises switch 111 which is configured to form a 1st and a 2nd current measurement paths so that current flows through the human body from one part of the body to another part of the body (from the AC source through one contact electrode to all other contact electrodes). To this end, the switch 111 comprises 4 ports 111-1, 111-2, 111-3, and 111-4. One of the ports (e.g., port 111-1) is connected to an AC source 120. An ammeter (A) 131 is connected to another port (e.g., to port 111-2). The remaining 2 ports (e.g., ports 111-3 and 111-4) are connected, respectively, to one of the contact electrodes intended for contacting with one part of the user's body (e.g., port 111-3 is connected to electrode 101), and to one of the contact electrodes intended for contacting with another part of the user's body (e.g., port 111-4 is connected to electrode 102). Thus, bioimpedance ($Z_b$) 160 (human body impedance) is connected between contact electrodes 101 and 102. The remaining 2 contact electrodes are connected to voltmeters (V) 141, 142—for example, the electrode 103 is connected to the first voltmeter (V1) 141, and the electrode 104 is connected to the second voltmeter (V2) 142. There is a corresponding contact impedance ($Z_{c1}$ ... $Z_{c4}$) 161, 162, 163, and 164 between each of electrodes 101-104 and bioimpedance ($Z_b$) 160. It should be noted that the AC source 120, the ammeter 131 and the voltmeters 141, 142 are also a part of the device. The AC source 120 and the ammeter 131 has common ground. The voltmeter 141 measures the voltage between electrode 103 and the common ground. The voltmeter 142 measures the voltage between the electrode 104 and the common ground.

The device 100 further comprises a processor 150 which is connected to the switch 111 to alternately form the 1st and the 2nd current measurement paths. Also, the processor 150 collects the current values measured by the ammeter 131 and the voltage values measured by the voltmeters 141, 142.

The device 100 may optionally be a part of another, more complex, user electronic device, which may also comprise other circuits and/or elements which are external to the device 100 and which may cause parasitic effects therein. All parasitic effects and external elements are combined for convenience in an equivalent circuit as parallel parasitic impedances connected to each contact electrode ($Z_{p1}$ ... $Z_{p4}$) 171, 172, 173, and 174, and serial parasitic impedances connected to each contact electrode ($Z_{s1}$ ... $Z_{s4}$) 181, 182, 183, and 184.

Figure 5A:
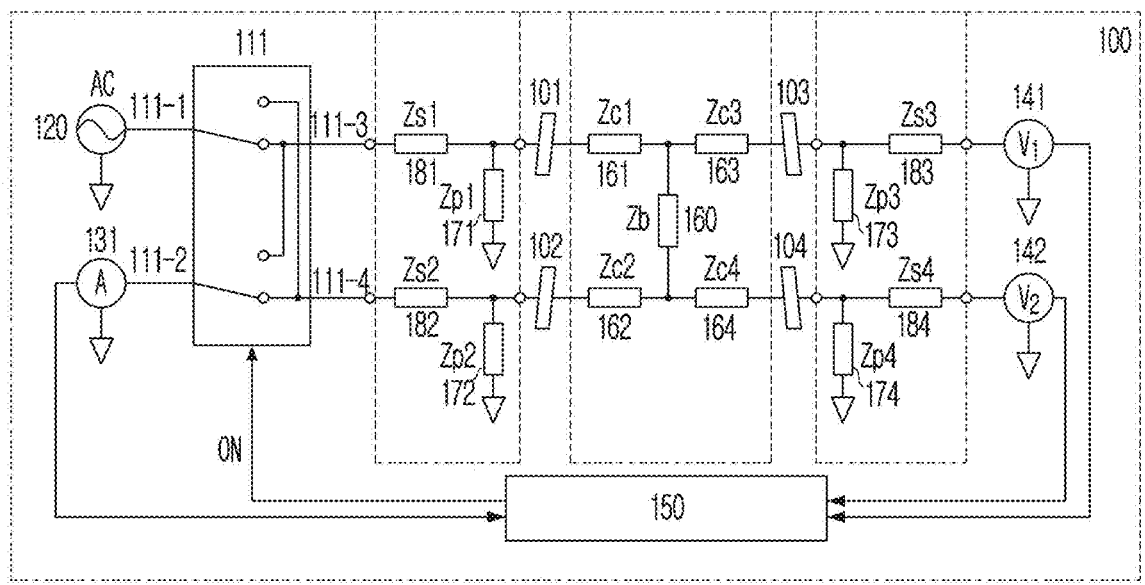
FIG. 5A shows the state of the device in which the switch forms the 1st current measurement path according to an embodiment of the disclosure.

FIG. 5A shows the state of the device in which the switch forms the 1st current measurement path according to an embodiment of the disclosure.

Further, FIG. 5A shows a state of the device 100, wherein the switch 111 forms the 1st current measurement path. The processor 150 sends a corresponding command to the switch 111 (e.g., the ON signal), and port 111-1 is connected to port 111-3, and port 111-2 is connected to port 111-4, so that the electrode 101 becomes electrically connected to the AC source 120, and the electrode 102 becomes electrically connected to the ammeter 131.

Figure 5B:
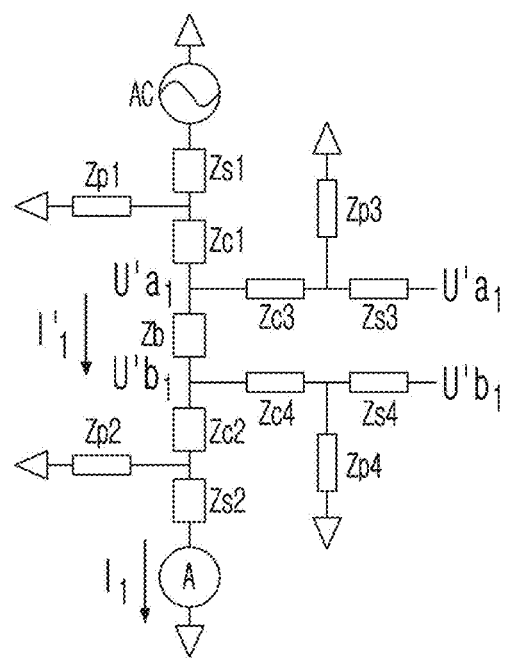
FIG. 5B shows the equivalent circuit of the 1st current measurement path according to an embodiment of the disclosure.

FIG. 5B shows the equivalent circuit of the 1st current measurement path according to an embodiment of the disclosure.

Referring to FIG. 5B, the processor 150 writes current value ($I_1$) of the ammeter 131 and voltage values ($U_{a1}$ ҳ $U_{b1}$) of the voltmeters 141, 142 according to an embodiment of the disclosure.

Figure 6A:
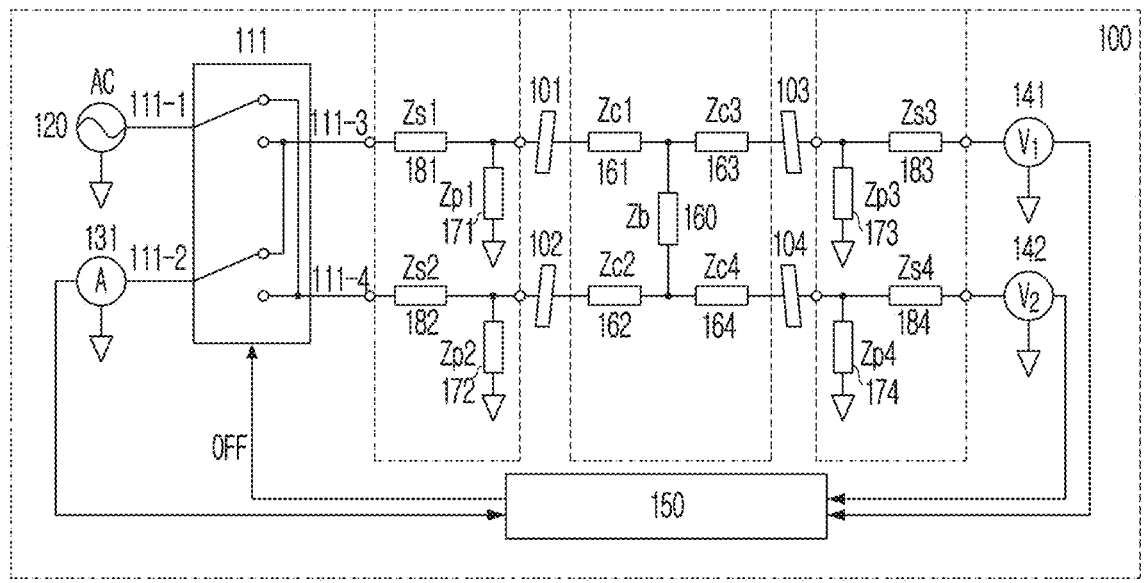
FIG. 6A shows the state of the device in which the switch forms the 2nd current measurement path according to an embodiment of the disclosure.

FIG. 6A shows the device state in which a switch forms the 2nd current measurement path according to an embodiment of the disclosure.

Referring to FIG. 6A, the processor 150 sends a corresponding other command to the switch 111 (e.g., an OFF signal), and port 111-1 is connected to port 111-4, and port 111-2 is connected to port 111-3, so that the electrode 101 becomes electrically connected to the ammeter 131, and the electrode 102 becomes electrically connected to the AC source 120.

Figure 6B:
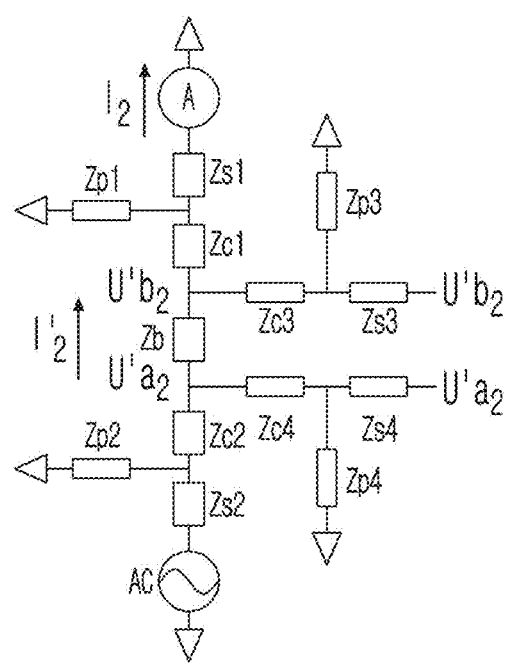
FIG. 6B shows the equivalent circuit of the 2nd current measurement path according to an embodiment of the disclosure.

FIG. 6B shows the equivalent circuit of the 2nd current measurement path according to an embodiment of the disclosure.

Referring to FIG. 6B, compared with FIG. 5B, the switch substantially only changes the AC source and the ammeter connections. The processor 150 writes the current value ($U_{a2}$ ҳ $U_{b2}$) of the voltmeters 141 and 142.

Then, by using the measured values of current and voltage, the processor calculates bioimpedance ($Z_b$) 160. The first current value ($I_1$), the first voltage value ($U_{a1}$) the 2-nd voltage value ($U_{b1}$), measured for the 1-st current measurement path, and the 2-nd current value ($I_2$), the 3-d voltage value ($U_{a2}$) and 4-th voltage value ($U_{b2}$), measured for the 2-d current measurement path, are used for calculating bioimpedance ($Z_b$) according to following formula:

$$Z_b = \frac{\dfrac{U_{a1}}{U_{b1}} - \dfrac{U_{b1}}{U_{a1}} + \dfrac{U_{a2}}{U_{b2}} - \dfrac{U_{b2}}{U_{a2}}}{I_1\left(\dfrac{1}{U_{a1}} + \dfrac{1}{U_{b1}}\right) + I_2\left(\dfrac{1}{U_{a2}} + \dfrac{1}{U_{b2}}\right)} \qquad \text{Equation 1}$$

Next, the calculation method will be explained in more detail.

Referring again to FIG. 5B, in and ideal case, if there were no parasitic and external components in the circuit, and contact impedance did not arise between the bioimpedance and the contact electrode, then only bioimpedance would remain in the entire equivalent circuit, voltage measurement would be carried out directly at the ends of the circuit, and the current measured in the circuit would flow only through the circuit, and then the calculation of the bioimpedance $Z_b$ when measured along the first current measurement path would be reduced to a simple formula, measuring voltages $U'_{a1}$ and $U'_{b1}$ would be performed directly at the ends of the circuit, and the current $I'_1$ measured in the circuit would flow only through the circuit, then the bioimpedance measurement, when measured at the first current measurement path ($Z_{bpath1}$), would be performed as follows:

$$Z_{bpath1} = \frac{U'_{a1} - U'_{b1}}{I'_1} \quad \text{Equation 2}$$

However, in real case, there is a number of parasitic and contact impedances between measurement points $U'_{a1}$ and $U'_{b1}$ and, correspondingly, $U_{a1}$ and $U_{b1}$. The voltage in the contact point $Z_{c3}$, $Z_{s3} \ltimes Z_{p3}$ is equal to voltage $U_{a1}$, since the current does not flow through $Z_{s3}$. Therefore $Z_{s3}$ can be omitted. Therefore, $$U_{a1}/Z_{p3} = U'_{a1}/(Z_{c3}+Z_{p3}) \quad \text{Equation 3}$$

A similar reasoning is valid for $U_{b1}$, $Z_{c4}$, $Z_{p4}$ and $Z_{s4}$.

Considering that the parallel parasitic impedance has a capacitive nature (this is due to the fact that usually the external (attached) component is characterized, namely, by the input capacitance, while its parallel resistance is large enough so that it can be ignored), the parallel parasitic impedance can be represented as $$Z_{pn} = \frac{1}{jwC_n} \quad \text{Equation 4}$$

wherein n—is an index of corresponding parasitic impedance on the circuit.

By substituting the real measured voltages into the above formula (2) for calculating the bioimpedance $Z_{bpath1}$, we get:

$$Z_{bpath1} = \frac{U_{a1}(1 + jwC_3Z_{c3}) - U_{b1}(1 + jwC_4Z_{c4})}{I'_1} \quad \text{Equation 5}$$

Further, by substituting the real measured current in the denominator, and expanding the brackets in the numerator, we get:

$$Z_{bpath1} = \frac{U_{a1} - U_{b1} + U_{a1}jwC_3Z_{c3} - U_{b1}jwC_4Z_{c4}}{I''_1 + I_1} \quad \text{Equation 6}$$

wherein $I''_1$— is the current that flows through the parasitic impedance.

Leaving only the current $I_1$ in the denominator, we get:

$$Z_{bpath1} = \frac{U_{a1} - U_{b1}}{I_1} + \frac{U_{a1}jwC_3Z_{c3} - U_{b1}jwC_4Z_{c4} - I''_1 Z_{bpath1}}{I_1} \quad \text{Equation 7}$$

Performing similar calculations for the 2nd current measurement path with reference to FIG. 6B, we get:

$$Z_{bpath2} = \frac{U'_{a2} - U'_{b2}}{I'_2} \quad \text{Equation 8}$$

$$Z_{bpath2} = \frac{U_{a2}(1 + jwC_4Z_{c4}) - U_{b2}(1 + jwC_3Z_{c3})}{I'_2} \quad \text{Equation 9}$$

-continued $$Z_{bpath2} = \frac{U_{a2} - U_{b2} + U_{a2}jwC_4Z_{c4} - U_{b2}jwC_3Z_{c3}}{I''_2 + I_2} \quad \text{Equation 10}$$

$$Z_{bpath2} = \frac{U_{a2} - U_{b2}}{I_2} + \frac{U_{a2}jwC_4Z_{c4} - U_{b2}jwC_3Z_{c3} - I''_2 Z_{bpath2}}{I_2}$$

Based on the measurements performed in the 1st and the 2nd current measurement paths, bioimpedance $Z_b$ can be represented as a weighted arithmetic mean of $Z_{bpath1}$ and $Z_{bpath2}$:

$$Z_b = \frac{A_1 Z_{bpath1} + A_2 Z_{bpath2}}{A_1 + A_2} \quad \text{Equation 12}$$

wherein $A_n$—are the weight factors of the weighted arithmetic mean:

$$A_n = \frac{I_n}{U_{an}} + \frac{I_n}{U_{bn}} \quad \text{Equation 13}$$

wherein n—a number of the measurement.

Thus, $$Z_b = \frac{Z_{bpath1}\left(\frac{I_1}{U_{a1}} + \frac{I_1}{U_{b1}}\right) + Z_{bpath2}\left(\frac{I_2}{U_{a2}} + \frac{I_2}{U_{b2}}\right)}{\frac{I_1}{U_{a1}} + \frac{I_1}{U_{b1}} + \frac{I_2}{U_{a2}} + \frac{I_2}{U_{b2}}} \quad \text{Equation 14}$$

By expanding, in equation (14), the values $Z_{bpath1}$ of formula (5), and $Z_{bpath2}$ of formula (11), equation (15) is obtained, which is common for calculating bioimpedance $Z_b$, using all components including parasitic and external.

$$Z_b = \frac{\left(\frac{U_{a1} - U_{b1}}{I_1} + \frac{U_{a1}jwC_3Z_{c3} - U_{b1}jwC_4Z_{c4} - I''_1 Z_{bpath1}}{I_1}\right)\left(\frac{I_1}{U_{a1}} + \frac{I_1}{U_{b1}}\right)}{\frac{I_1}{U_{a1}} + \frac{I_1}{U_{b1}} + \frac{I_2}{U_{a2}} + \frac{I_2}{U_{b2}}} + \frac{\left(\frac{U_{a2} - U_{b2}}{I_2} + \frac{U_{a2}jwC_4Z_{c4} - U_{b2}jwC_3Z_{c3} - I''_2 Z_{bpath2}}{I_2}\right)\left(\frac{I_2}{U_{a2}} + \frac{I_2}{U_{b2}}\right)}{\frac{I_1}{U_{a1}} + \frac{I_1}{U_{b1}} + \frac{I_2}{U_{a2}} + \frac{I_2}{U_{b2}}} \quad \text{Equation 15}$$

If assumed is, that in equation (15):

the part associated with directly measured current and voltage values characterizes the estimated value of bioimpedance $Z'_b$ which for the purposes of the disclosure can be taken as the desired value instead of obtaining the true bioimpedance value $Z_b$, and the rest part, in which required is to consider the parasitic and external components, characterizes the error $Z_{error}$ introduced by them, the following is obtained:

$$Z_b = Z'_b Z_{error} \quad \text{Equation 16}$$

wherein $$Z'_b = \frac{\frac{U_{a1}}{U_{b1}} - \frac{U_{b1}}{U_{a1}} + \frac{U_{a2}}{U_{b2}} - \frac{U_{b2}}{U_{a2}}}{I_1\left(\frac{1}{U_{a1}} + \frac{1}{U_{b1}}\right) + I_2\left(\frac{1}{U_{a2}} + \frac{1}{U_{b2}}\right)} \quad \text{Equation 17}$$

$$Z_{error} = \frac{\left(\frac{U_{a1}}{U_{b1}} - \frac{U_{b2}}{U_{a2}}\right)jwC_3Z_{c3} + \left(\frac{U_{a2}}{U_{b2}} - \frac{U_{b1}}{U_{a1}}\right)jwC_4Z_{c4} - I''_1 Z_{bpath1}\left(\frac{1}{U_{a1}} + \frac{1}{U_{b1}}\right) - I''_2 Z_{bpath2}\left(\frac{1}{U_{a2}} + \frac{1}{U_{b2}}\right)}{I_1\left(\frac{1}{U_{a1}} + \frac{1}{U_{b1}}\right) + I_2\left(\frac{1}{U_{a2}} + \frac{1}{U_{b2}}\right)}$$

The error introduced into $Z_b$ in formula (16) by value $Z_{error}$, can be estimated as $$\Delta Z_b = \left|1 - \frac{Z'_b}{Z_b}\right| \quad \text{Equation 18}$$

To obtain an accurate bioimpedance value, the value $Z_{error}$ should be small enough in relation to $Z_b$ (acceptable maximum error for compact electronic devices is ~10-20% for contact impedances up to 50 kΩ). $Z_{error}$ may be estimated by means of modeling based on the data available to the authors, obtained as a result of measurements carried out on professional equipment for multiple users, as well as obtained as a result of calibrating multiple compact devices that have the BIA function.

Suppose two electrodes 102 and 104 are connected to a wrist. Based on the authors data, the contact impedance in the wrist region has following typical values:
 minimal values mag($Z_{c2}$) and mag($Z_{c4}$) are 0.2 kOhm.
 maximum values mag($Z_{c2}$) and mag($Z_{c4}$) are 20 kOhm.
 minimal values arg($Z_{c2}$) and arg($Z_{c4}$) are −70 degrees.
 maximum values arg($Z_{c2}$) and arg($Z_{c4}$) are −40 degrees.
 Here, mag—is an absolute value (magnitude), arg-phase.
Further assuming that other two electrodes 101 and 103 are connected to fingers. Based on the authors data, the contact impedance at the fingers takes the following typical values:
 minimal values mag($Z_{c1}$) and mag($Z_{c3}$) are 0.5 kOhm.
 maximum values mag($Z_{c1}$) and mag($Z_{c3}$) are 50 kOhm.
 minimal values arg($Z_{c1}$) and arg($Z_{c3}$) are −70 degrees.
 maximum values arg($Z_{c1}$) and arg($Z_{c3}$) are −40 degrees.
Based on the authors data, it can be assumed that typical values of parallel parasitic impedances ($Z_{p1}$ . . . $Z_{p4}$) range from 0 pF to 150 pF.

It can also be assumed that the minimum values of the serial parasitic impedances ($Z_{s1}$ . . . $Z_{s4}$) are equal to 1 kOhm.

Figure 7A:
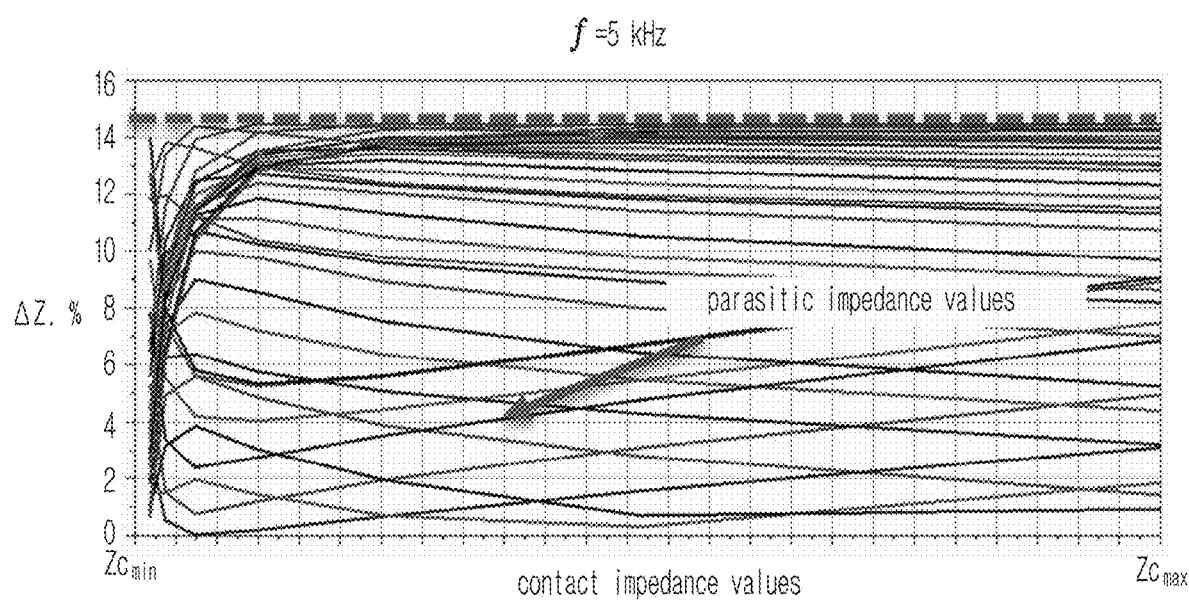
FIGS. 7A, 7B, and 7C show the results of simulated introduced error values depending on different parasitic component values and contact impedances for different frequencies according to various embodiments of the disclosure.
Figure 7B:
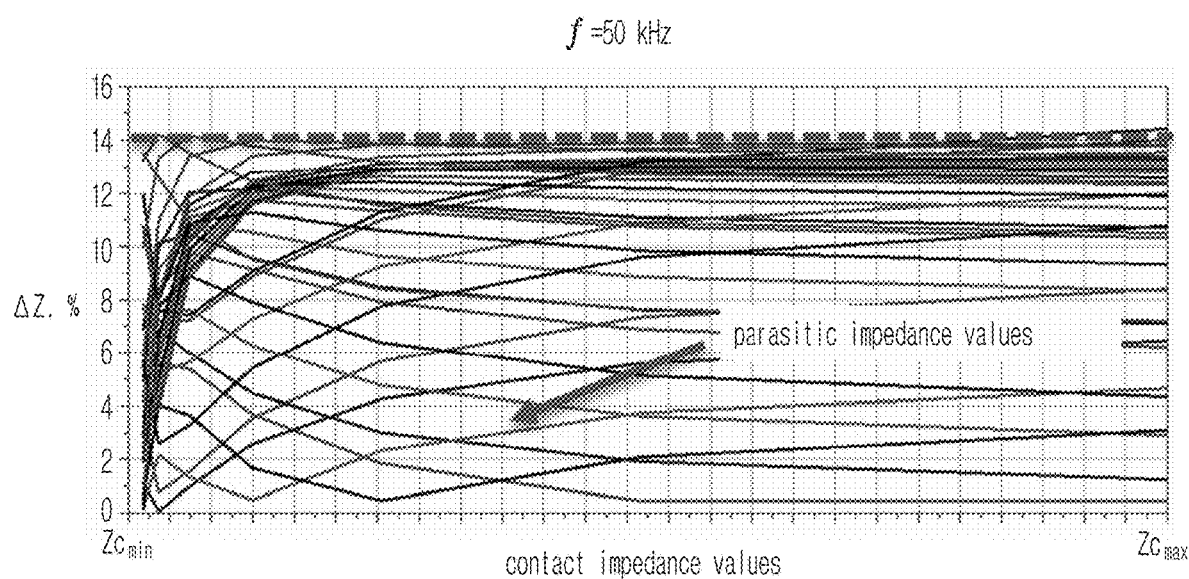
Figure 7C:
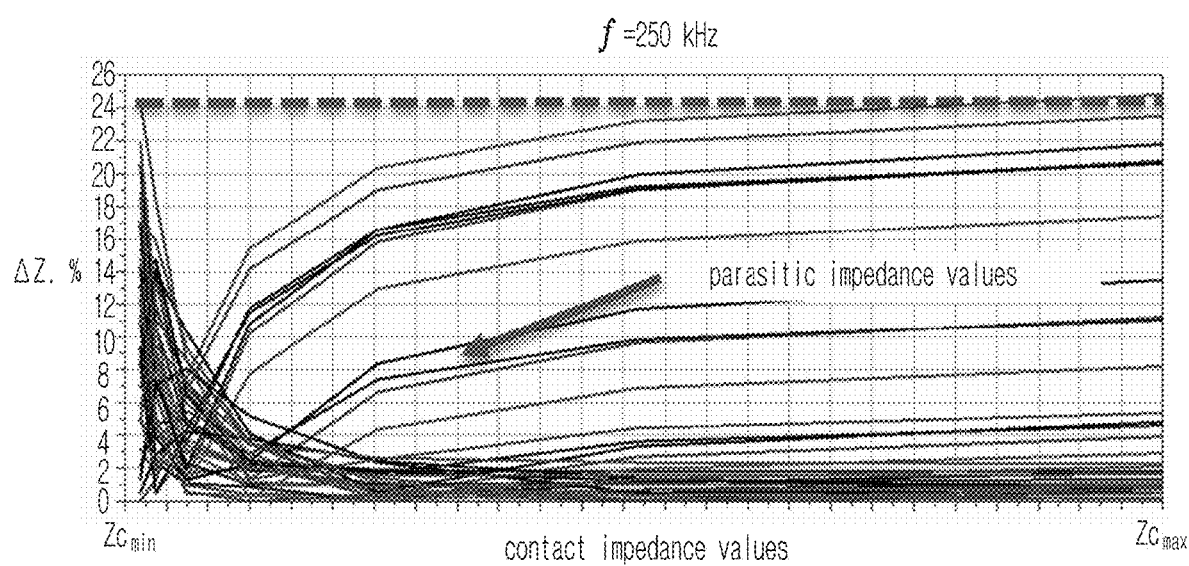

FIGS. 7A, 7B, and 7C show simulation results of introduced error values $$\left(\Delta Z_b = \left|1 - \frac{Z'_b}{Z_b}\right|\right)$$

depending on different values of the parasitic components and contact impedances for different frequencies according to various embodiments of the disclosure.

Referring to FIGS. 7A to 7C, the impedance values are normalized so that their respective ranges fit on the same graph. As shown in FIG. 7A for 5 kHz, no matter how the parasitic components and contact impedances change within the above typical values, the maximum introduced error is ~14%. FIG. 7B shows that for a frequency of 50 kHz, the maximum introduced error is ~14% for the above typical ranges. FIG. 7C shows that the maximum introduced error is ~24% for a frequency of 250 kHz.

Figure 8:
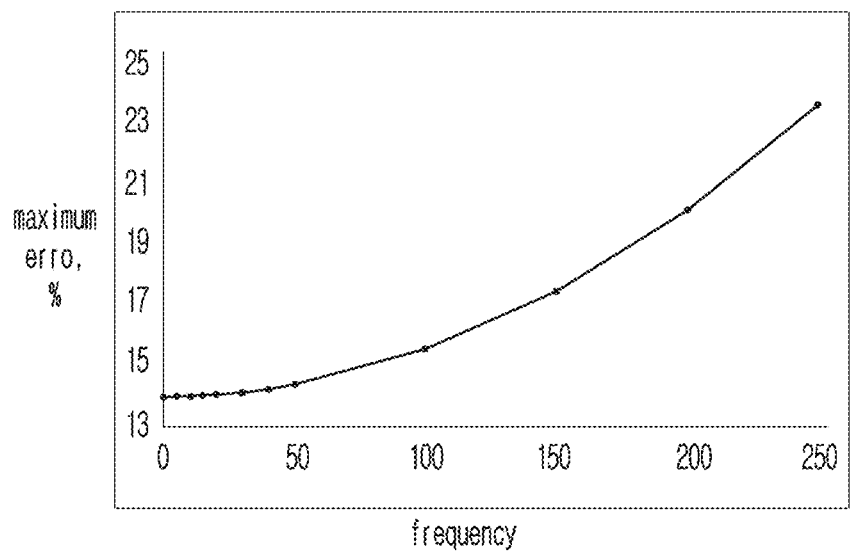
FIG. 8 is a graph showing the maximum error in dependence of frequency according to an embodiment of the disclosure.

FIG. 8 is a graph of the maximum error introduced by $Z_{error}$, depending on frequency according to an embodiment of the disclosure.

Referring to FIG. 8, at a measurement frequency of 50 kHz, typical for compact wearable devices, the maximum introduced error is ~14%. Further, with increasing the frequency, the maximum error value increases.

Accordingly, in the above equation (16), the introduced error is acceptable for estimating the body impedance.

The following describes in more detail how to perform correction of the estimated value of bioimpedance $Z'_b$ to obtain a corrected value of bioimpedance $Z_{bcorr}$ according to an embodiment of the disclosure. By performing bioimpedance measurements for multiple users (of the control sample) with high-precision professional medical devices, possible is to obtain a database with reference values $Z_{bref}$ for each user. By performing bioimpedance measurements for the same plurality of users with the device of the disclosure, a database of estimated values $Z'_b$) can be obtained for each user. With these two databases, linear regression of the results can be performed in order to minimize the estimation error. Possible are various embodiments for implementing this approach.

In one embodiment, the correction can be made using the following equation:

$$Z_{bcorr} = w_0 + w_1 |Z'_b| + w_2 \arg(Z'_b) \quad \text{Equation 19}$$

wherein $w_0$, $w_1$, $w_2$—are weight factors.

Expanding value $Z'_b$ in this formula, the equation can be presented as follows:

$$Z_{bcorr} = w_0 + w_1 \left|\frac{\frac{U_{a1}}{U_{b1}} - \frac{U_{b1}}{U_{a1}} + \frac{U_{a2}}{U_{b2}} - \frac{U_{b2}}{U_{a2}}}{I_1\left(\frac{1}{U_{a1}} + \frac{1}{U_{b1}}\right) + I_2\left(\frac{1}{U_{a2}} + \frac{1}{U_{b2}}\right)}\right| + w_2 \arg\left(\frac{\frac{U_{a1}}{U_{b1}} - \frac{U_{b1}}{U_{a1}} + \frac{U_{a2}}{U_{b2}} - \frac{U_{b2}}{U_{a2}}}{I_1\left(\frac{1}{U_{a1}} + \frac{1}{U_{b1}}\right) + I_2\left(\frac{1}{U_{a2}} + \frac{1}{U_{b2}}\right)}\right) \quad \text{Equation 20}$$

The weight factors $w_0$, $w_1$, $w_2$ can be obtained using linear regression using the machine learning (ML) method, for example, using a model aimed at minimizing the mean square error. In particular, in ML there is a selection of the most suitable values of the coefficients $w_0$, $w_1$, $w_2$ based on minimizing the mean square error between the real value of the dependent variable taken from the training database and a prediction produced by the model.

The obtained correction formula can be used in the device itself for any user.

By way of example only, and not limitation, the following is a specific variant of the correction formula for this embodiment, obtained for a test sample of approximately 3000 users, whose bioimpedances were measured in the manner proposed above, that is, both on professional equipment and using the device described in the disclosure.

$$Z_{bcorr} = -40.2(O_M) + 1.18*|Z'_b| - 8.18(O_M/\text{градус})*\arg(Z'_b) \quad \text{Equation 21}$$

Figure 9:
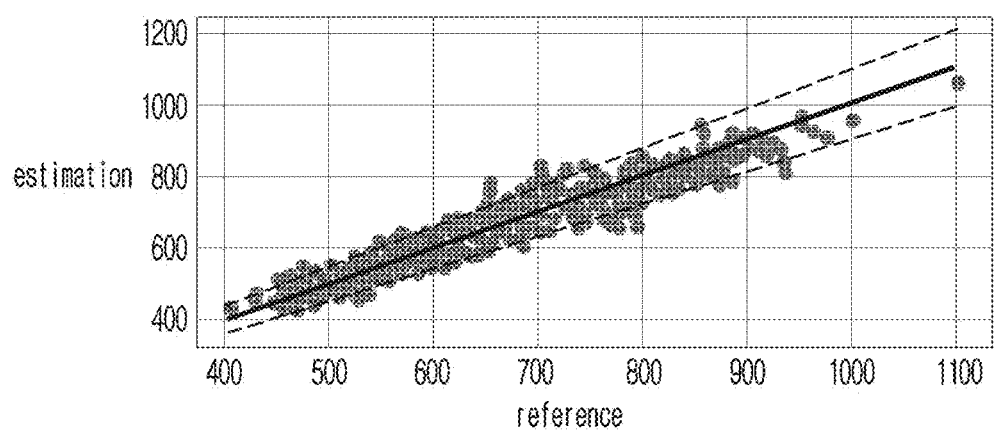
FIG. 9 is a schematic representation of a linear regression graph for a test sample example according to an embodiment of the disclosure.

FIG. 9 is a schematic representation of a linear regression graph for a test sample example according to an embodiment of the disclosure.

Referring to FIG. 9, a corresponding schematic representation of a linear regression graph for this test sample example is, where the Y-axis represents the reference bioimpedance values and the X-axis represents the estimated values.

Figure 10:
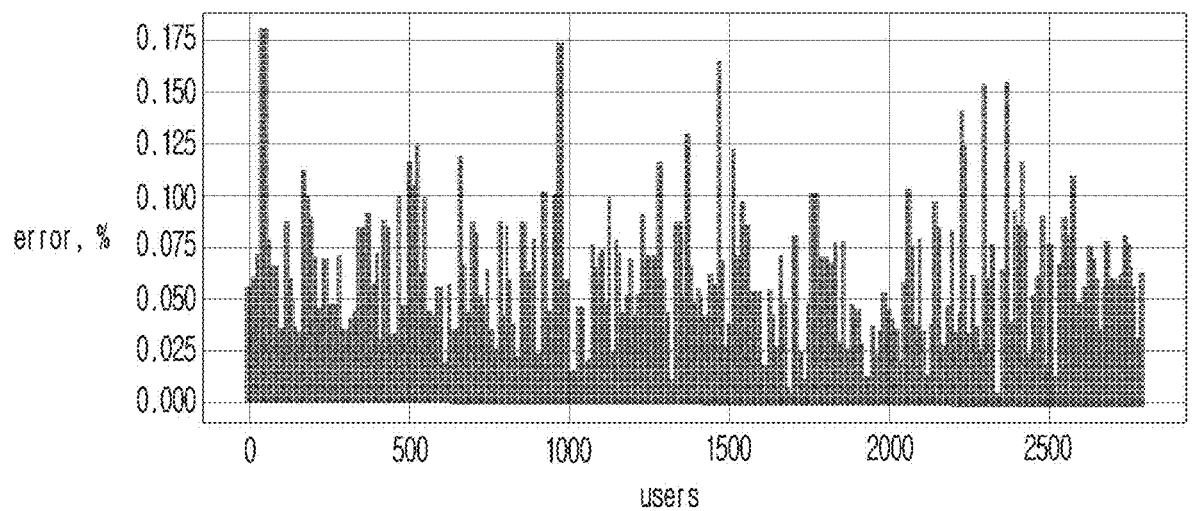
FIG. 10 is a graph of the error between the corrected value of FIG. 9 and a reference value for each user from the test sample according to an embodiment of the disclosure.

FIG. 10 shows a graph of the resulting error between the corrected value $Z_{bcorr}$ the reference value $Z_{bref}$ for each user from the test sample according to an embodiment of the disclosure.

Referring to FIG. 10, the correlation of the correction results obtained in this way with the reference values is high, in particular, the determination coefficient is 0.943 in this example. At the same time, the error for 99% of users does not exceed 11.2% and even in the worst single cases does not exceed 18%. Accordingly, due to the correction, a more accurate result can be obtained by linear regression to the impedance database collected by the reference medical device. It should be understood that the larger and more representative the sample, the higher the accuracy of the regression model and the correction made.

In another embodiment, the correction can be made using the following formula:

$$Z_{bcorr} = w_0 + w_1\, \text{re}(Z'_b) + w_2\, \text{im}(Z'_b) \quad \text{Equation 22}$$

Similar to the previous embodiment, the weight factors $w_0$, $w_1$, $w_2$ can be obtained using linear regression by the ML method, and then the obtained correction formula can be used in the device itself, applying it to any users.

In one more embodiment, further to direct reference values $Z_{bref}$ and estimated valued $Z'_b$, additional data about the user can be introduced into the database for each user, which affect the bioimpedance in one way or another, for example, data on weight, height, age and gender of each user. With such data, linear regression of the results can be performed in order to minimize the estimation error.

In general, for such embodiment, the linear regression correction can be represented as follows:

$$Z_{bcorr} = w_0 + w_1|Z'_b| + w_2\arg(Z'_b) + w_3 W + w_4 H + w_5 A + w_6 G \quad \text{Equation 23}$$

wherein $w_0$, $w_1$, $w_2$, $w_3$, $w_4$, $w_5$, $w_6$—are weight factors,
W—user's weight,
H—user's height,
A—user's age,
G—user's gender.

In an illustrative embodiment, W, H, and A values may be measured in standard units, and G may be 0 or 1. Weight factors $w_0$, $w_1$, $w_2$, $w_3$, $w_4$, $w_5$, $w_6$ can be obtained using linear regression by the machine learning (ML) method, for example, using a model aimed at minimizing the mean square error. Then the obtained correction formula can be used in the device itself for any user.

As a non-limiting example, the following is a specific version of the correction formula for this embodiment, obtained for a test sample of approximately 3000 users, for whom bioimpedances were measured on professional equipment and using the device described in the disclosure, and also indicates the weight, height, age, and gender:

$$Z_{bcorr} = -33.9(O_M) + 1.017*|Z'_b| - \\ 6.54\left(\frac{O_M}{\text{градус}}\right)*\arg(Z'_b) - 1.16\left(\frac{O_M}{\text{кг}}\right)*W + \quad \text{Equation 24}$$

-continued
$$1.19\left(\frac{O_M}{M}\right)*H - 0.08\left(\frac{O_M}{\text{год}}\right)*A - 20.9(O_M)*G$$

wherein G is 0, if the user is a woman, or 1 if the user is a man.

Figure 11:
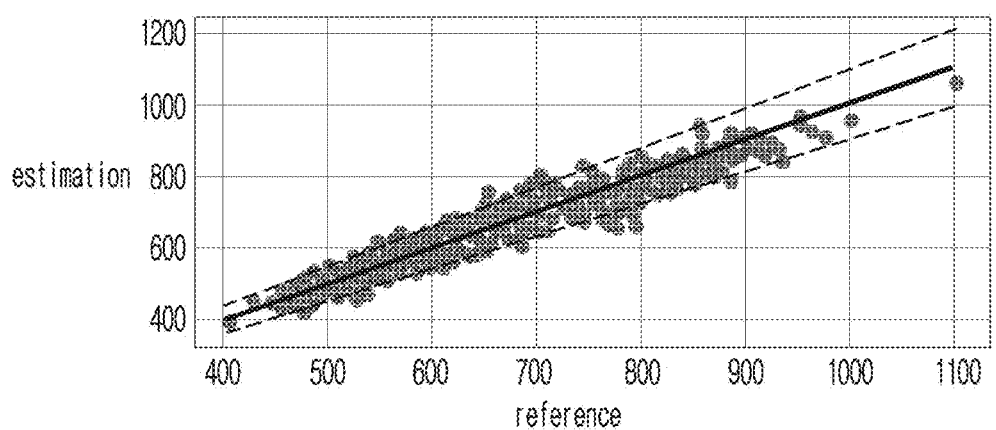
FIG. 11 is a schematic representation of a linear regression graph for another test sample example according to an embodiment of the disclosure.

FIG. 11 is a schematic representation of a linear regression graph for another test sample example according to an embodiment of the disclosure.

Figure 12:
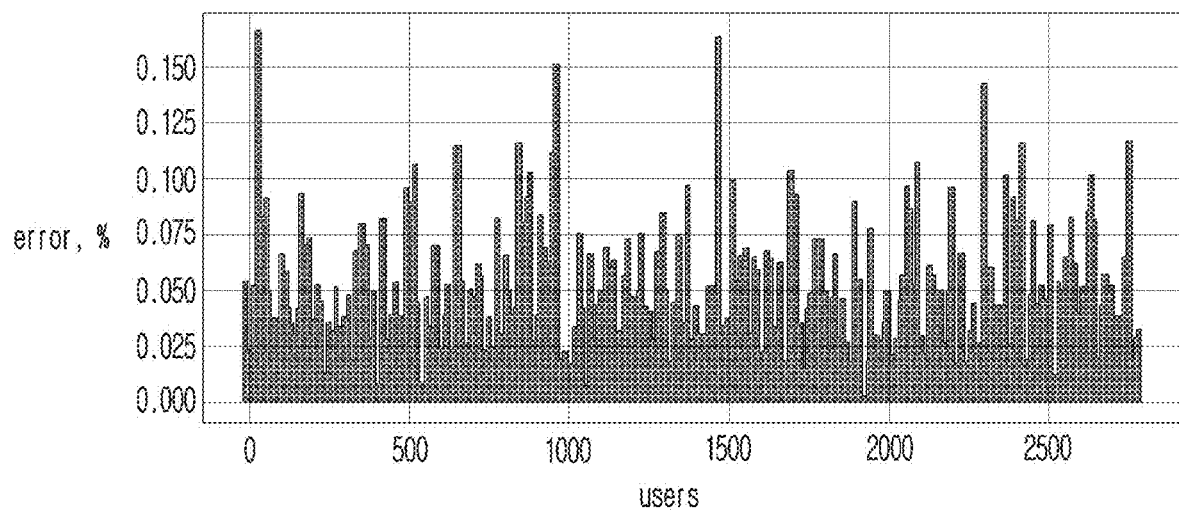
FIG. 12 is a graph of the error between the corrected value of FIG. 11 and a reference value for each user from the test sample according to an embodiment of the disclosure.

FIG. 12 is a graph of the error between the corrected value of FIG. 11 and a reference value for each user from the test sample according to an embodiment of the disclosure.

A corresponding schematic representation of a linear regression graph for this test sample example is shown in FIG. 11, where the Y-axis represents the reference values of bioimpedance and the X-axis represents the estimated values. FIG. 12 shows a graph of the error obtained in such case between the corrected value $Z_{bcorr}$ and the reference value $Z_{bref}$ for each user from the test sample, taking into account the user's profile (weight, height, age, gender). The correlation of the correction results obtained in this way with the reference values is even higher than in the previous embodiment, in particular, the coefficient of determination in this example is 0.965. While, the error for 99% of users does not exceed 8.9% and even in the worst single cases does not exceed 16.5%. Accordingly, by correcting for the user profile, an even more accurate result can be obtained by linear regression to the impedance database collected by the reference medical device. It should be understood that the larger and more representative the sample, the higher the accuracy of the regression model and the correction made. It should also be understood that not all of the specified user profile parameters may be used in a particular implementation of the disclosure. If necessary, in addition to or instead of any of the above parameters, other parameters can be used, such as race, waist circumference, hip circumference, wrist circumference, etc.

In another embodiment, the correction can be made using the following formula:

$$Z_{bcorr} = w_0 + w_1\,\text{re}(Z'_b) + w_2\,\text{im}(Z'_b) + w_3 W + w_4 H + w_5 A + \\ w_6 G \quad \text{Equation 25}$$

Similar to the previous embodiment, weight factors $w_0$, $w_1$, $w_2$, $w_3$, $w_4$, $w_5$, $w_6$ can be obtained using linear regression by the ML method, and then the obtained correction formula can be used in the device itself, with applying it to any users.

Figure 13:
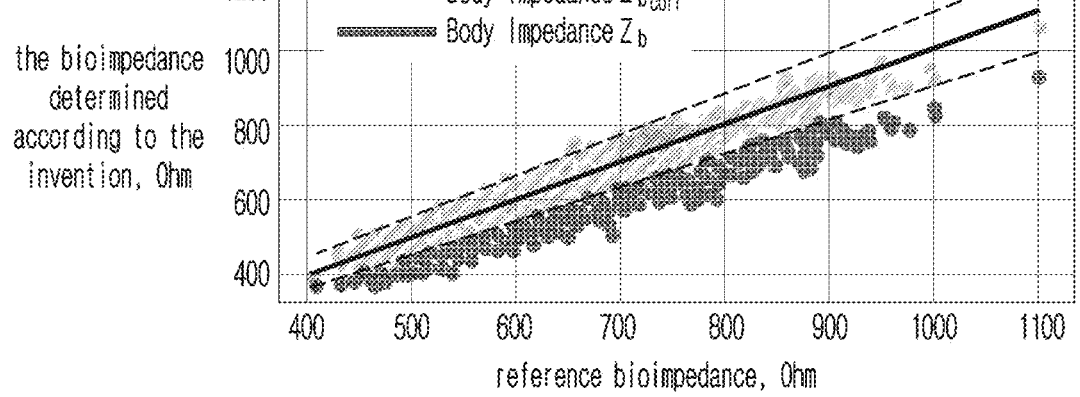
FIG. 13 is a summary graph comparing bioimpedance determination results with reference measurement results according to an embodiment of the disclosure.

FIG. 13 is a summary graph comparing bioimpedance determination results with reference measurements of impedance using professional equipment for a plurality of users according to an embodiment the disclosure.

Referring to FIG. 13, the Y-axis represents estimated values (red dots) and corrected values $Z_{bcorr}$ (blue dots), and the X-axis represents the reference bioimpedance values. The maximum error in determining bioimpedance according to the disclosure does not exceed 15% compared to reference medical equipment.

Figure 14:
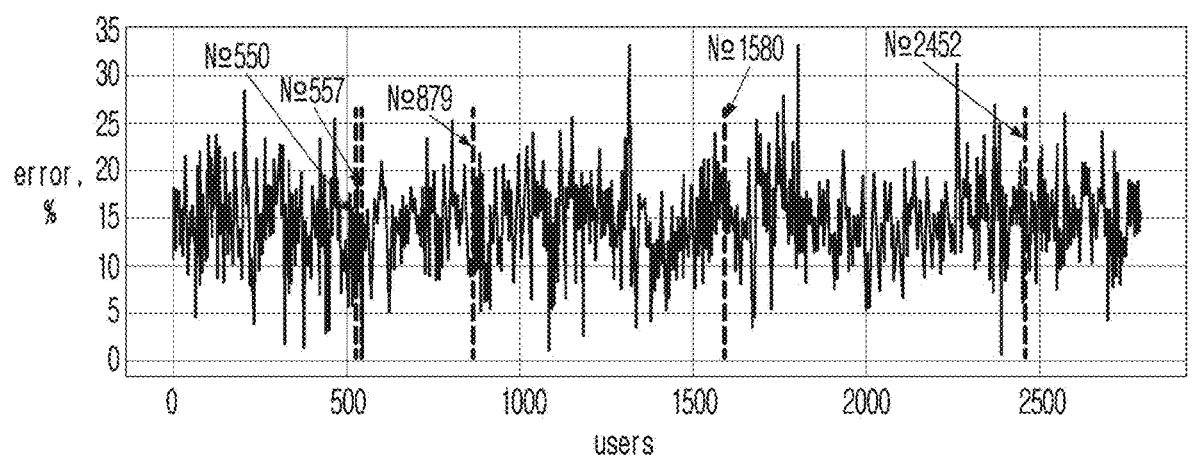
FIG. 14 is a graph comparing bioimpedance determination errors for multiple users according to an embodiment of the disclosure.

FIG. 14 is a graph of comparison of bioimpedance determination errors for multiple users, which shows how the accuracy of calculating body impedance in the disclosure changes in the case where the block B (parasitic and external components) is not taken into account (blue line) compared to the case when the block B is taken into account (red line) according to an embodiment the disclosure.

Referring to FIG. 14, in both cases, all errors have an extremely high correlation and the same average rate for all users—about 15%, which is acceptable accuracy for a compact wearable device. Even for users with high contact impedance of the skin, the error in determining the impedance of the body does not exceed 25-33%.

Thus, the embodiments of the disclosure achieve the same or even better accuracy compared to reference bioimpedance values (measured by professional equipment) as many other compact wearable devices, but unlike other wearable devices, does not require calculation or knowledge of contact impedances, as well as parasitic and external elements.

Moreover, it should be considered that all of the above detailed description has been related to the structure of the device for detecting human body impedance shown in FIG. 4. Therefore, in order to obtain an acceptable accuracy in determining the bioimpedance, the disclosure is weakly dependent on the frequency of the signal generator and does not require a complex switch, such as a 4×4 matrix for making 8 different measurements, but in a necessary and sufficient way includes only one switch configured to perform 2 different measurements.

The above description corresponds to a preferred embodiment of the device for bioimpedance measuring according to the disclosure. Further embodiments will be described below.

Figure 15:
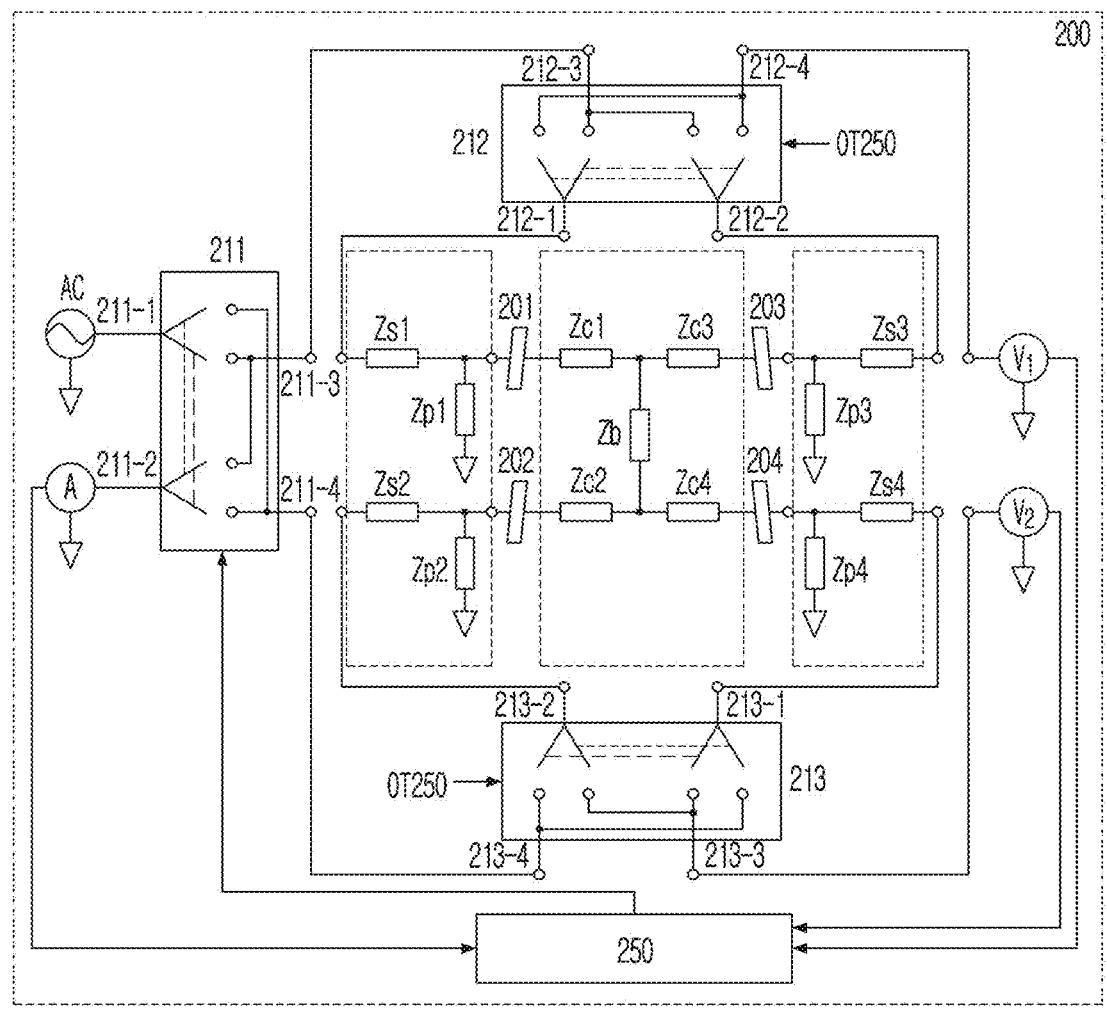
FIG. 15 shows a further embodiment of the bioimpedance measurement device according to an embodiment of the disclosure.
Figure 16A:
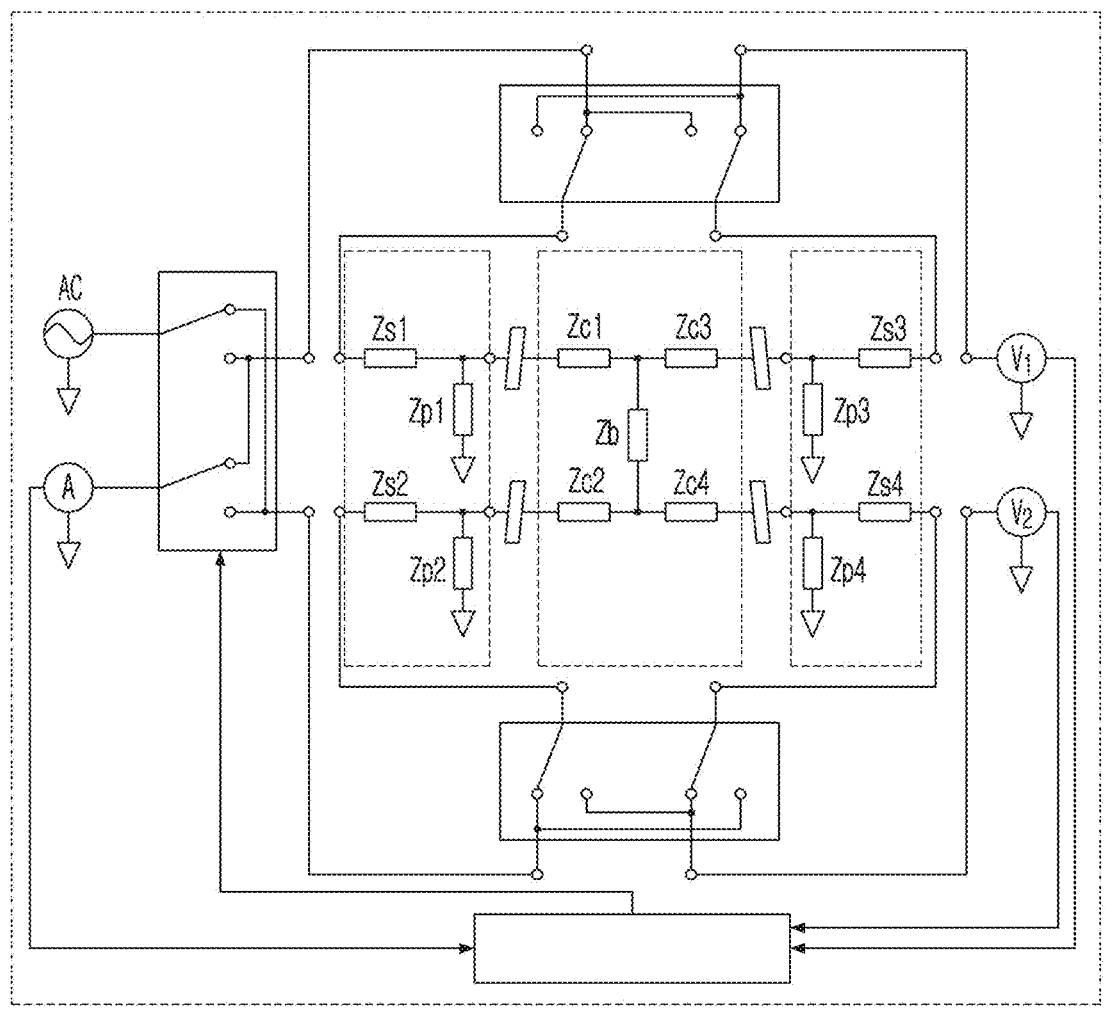
FIGS. 16A, 16B, 16C, and 16D show current measurement paths for the embodiment of FIG. 15 according to various embodiments of the disclosure.
Figure 16B:
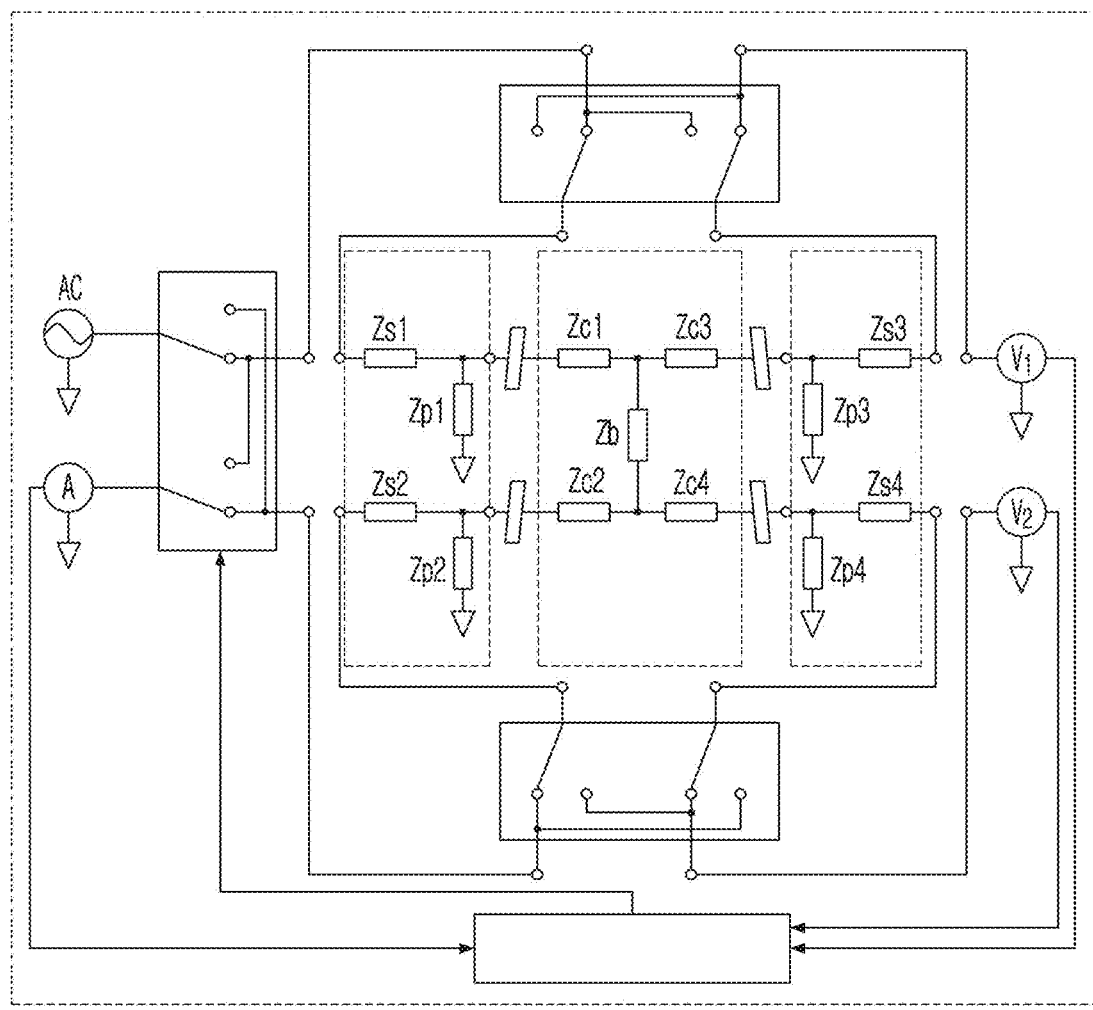
Figure 16C:
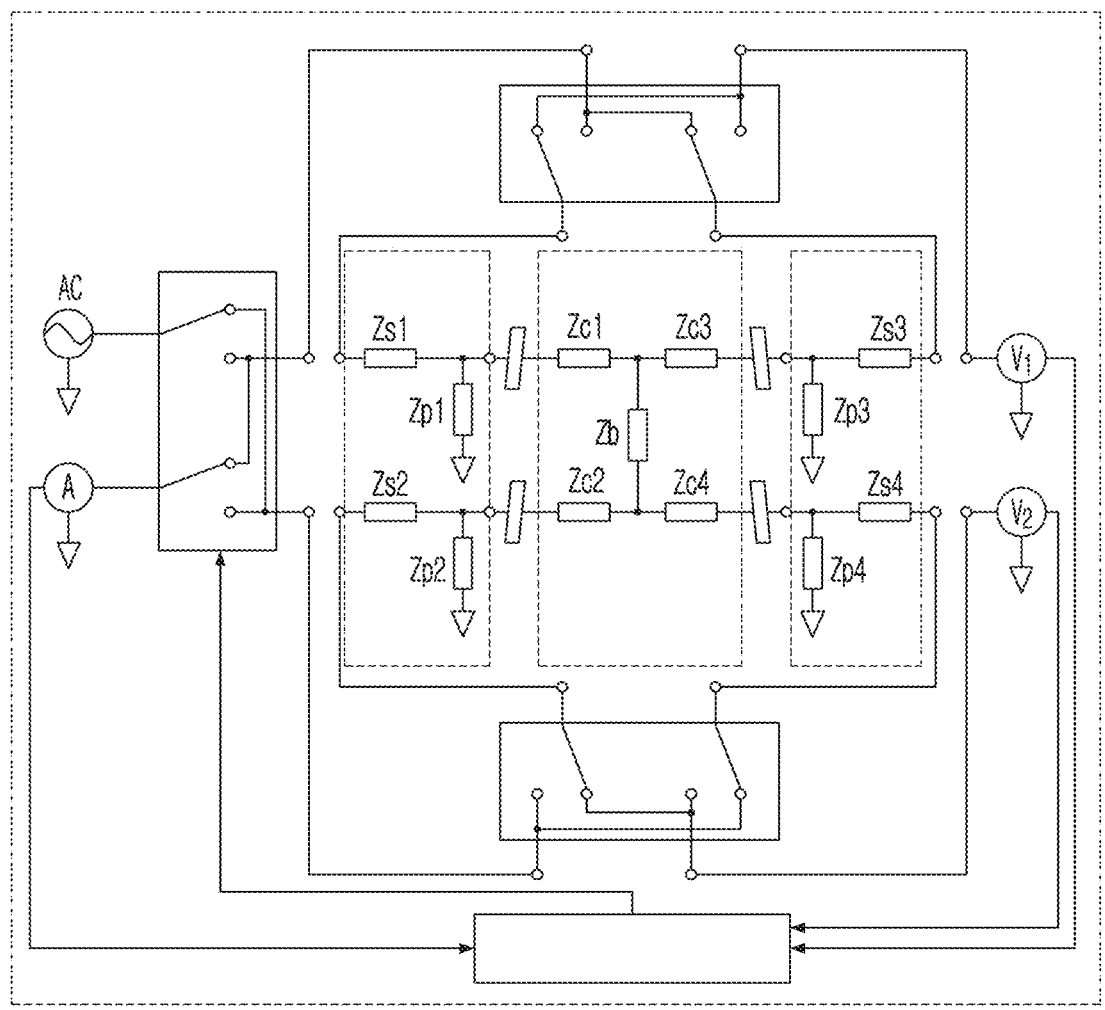
Figure 16D:
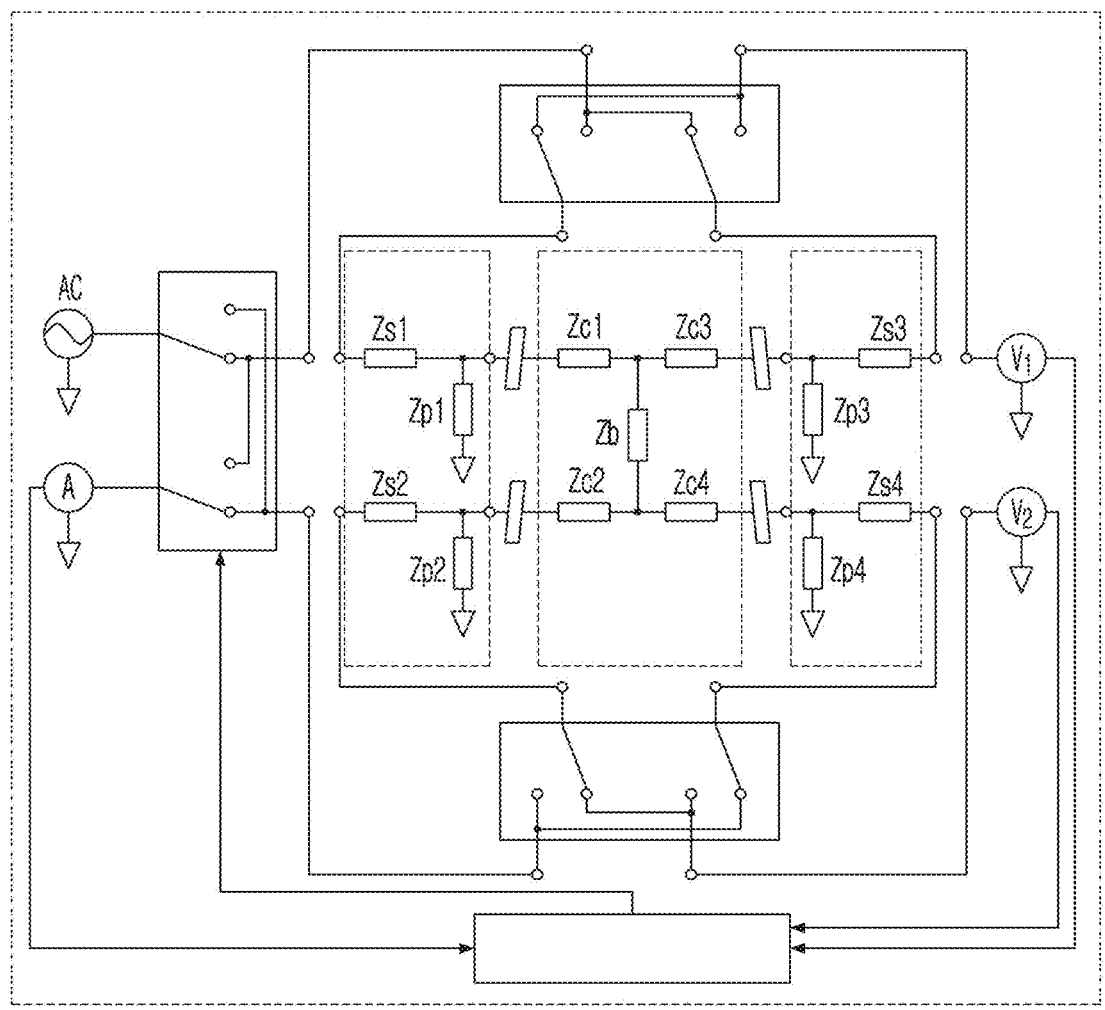

FIG. 15 shows a further embodiment of the bioimpedance measurement device according to an embodiment of the disclosure.

FIGS. 16A, 16B, 16C, and 16D show current measurement paths for the embodiment of FIG. 15 according to various embodiments of the disclosure.

FIG. 15 shows an embodiment of a bioimpedance measuring device 200, wherein unlike the device 100 shown in FIG. 4, 2 additional switches (212, 213) are applied according to an embodiment of the disclosure. Each of the switches 212 and 213 have corresponding ports 212-1 to 212-4 and 213-1 to 213-4. A description of those elements of FIG. 15 that correspond to elements of FIG. 4, such as electrodes 201 to 204, switch 211, ports 211-1 to 211-4, and processor 250 is omitted. This structure allows to configure 4 current measurement paths (shown, respectively, in FIGS. 16A, 16B, 16C, and 16D). As a result, due to four measurements, a more accurate bioimpedance determination result can be obtained using the following formula:

$$Z_b = \frac{\frac{U_{a1}}{U_{b1}} - \frac{U_{b1}}{U_{a1}} + \frac{U_{a2}}{U_{b2}} - \frac{U_{b2}}{U_{a2}} + \frac{U_{a3}}{U_{b3}} - \frac{U_{b3}}{U_{a3}} + \frac{U_{a4}}{U_{b4}} - \frac{U_{b4}}{U_{a4}}}{I_1\left(\frac{1}{U_{a1}} + \frac{1}{U_{b1}}\right) + I_2\left(\frac{1}{U_{a2}} + \frac{1}{U_{b2}}\right) + I_3\left(\frac{1}{U_{a3}} + \frac{1}{U_{b3}}\right) + I_4\left(\frac{1}{U_{a4}} + \frac{1}{U_{b4}}\right)} \quad \text{Equation 26}$$

Figure 17:
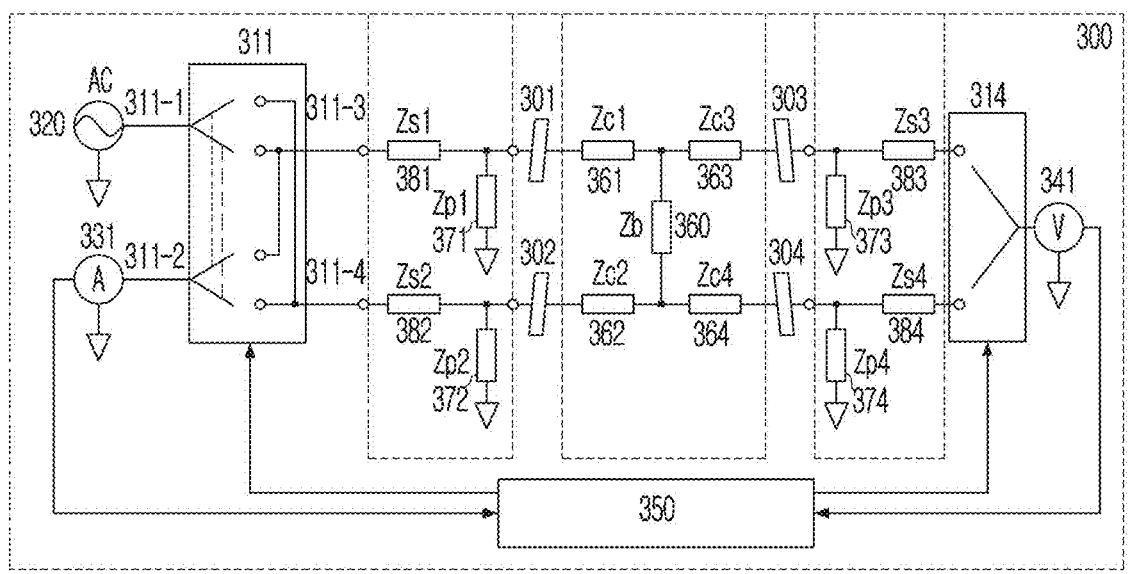
FIG. 17 shows another additional embodiment of the bioimpedance measurement device disclosure according to an embodiment of the disclosure.
Figure 18A:
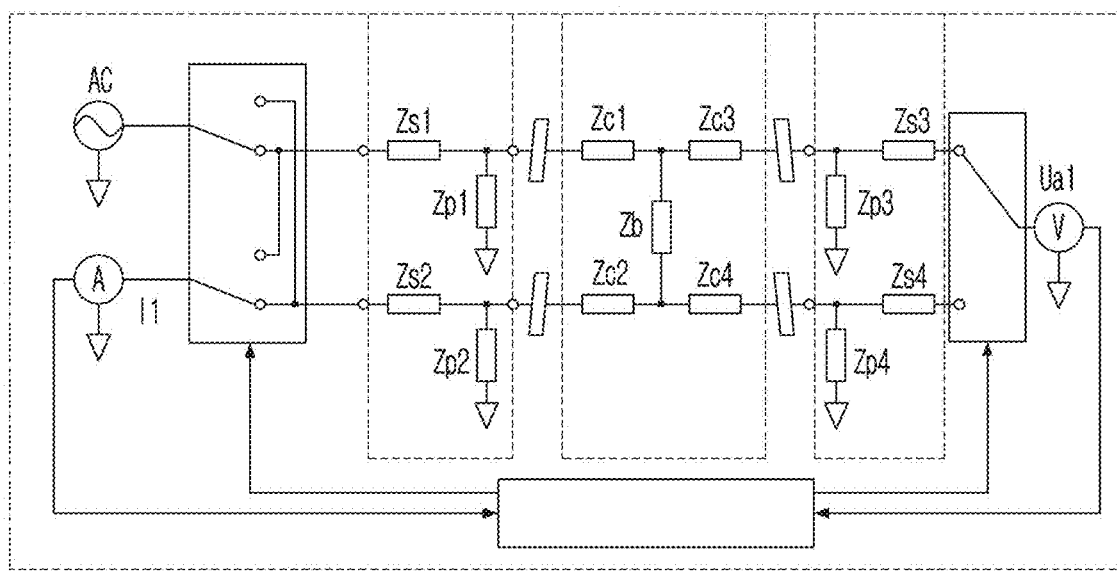
FIGS. 18A, 18B, 18C, and 18D show current measurement paths for the embodiment of FIG. 17 according to various embodiments of the disclosure.
Figure 18B:
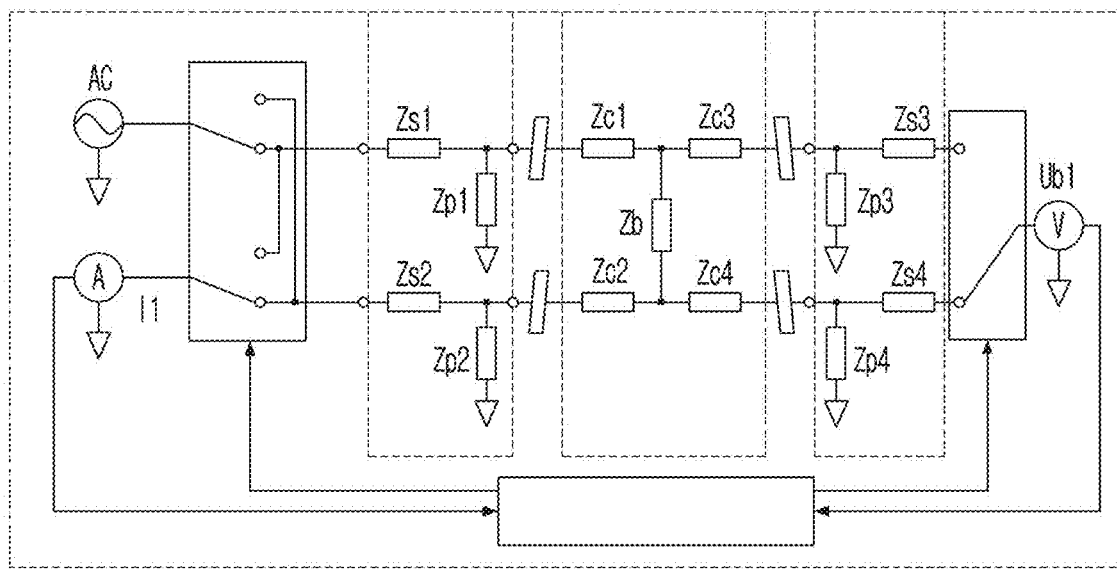
Figure 18C:
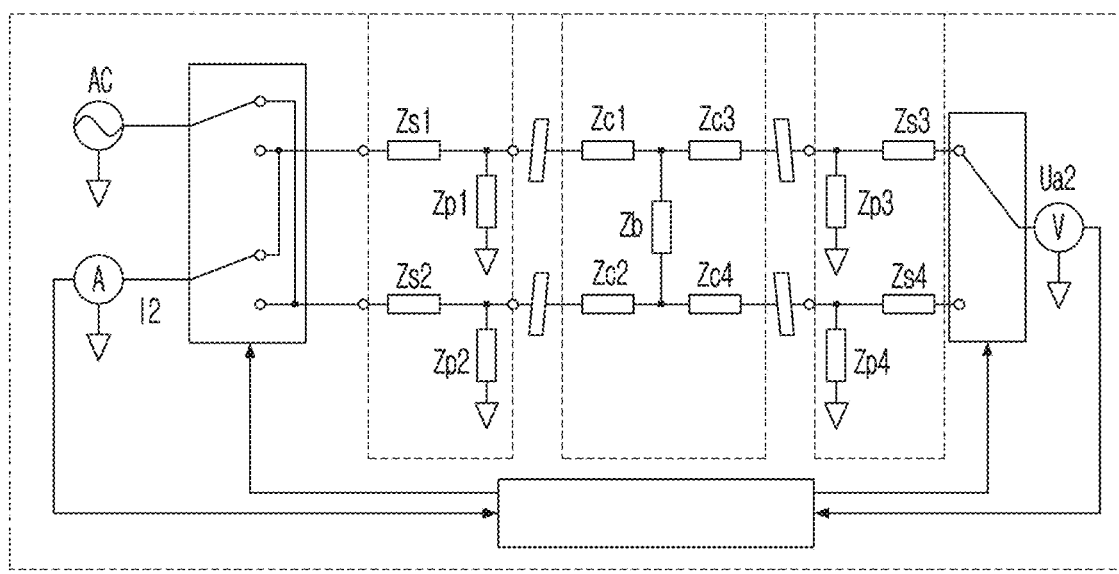
Figure 18D:
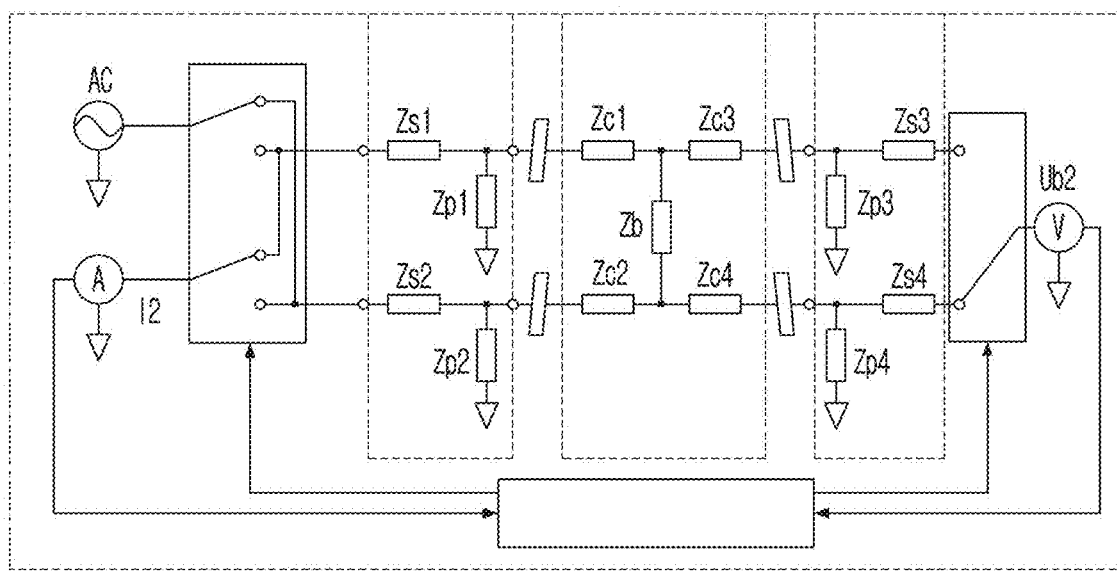

FIG. 17 shows another additional embodiment of the bioimpedance measurement device disclosure according to an embodiment of the disclosure.

FIG. 17 shows an embodiment of a bioimpedance measuring device 300, wherein unlike the device 100 shown in FIG. 4, 1 additional switch (314) is applied, also connected to and controlled by the processor. This structure allows one voltmeter (341) to be used instead of two. To do this, each of the contact electrodes 303 and 304 in each of the 1st and the 2nd current measurement paths shall be connected to one voltmeter using switch 314. Corresponding current measurement paths 1a (for measuring $I_1$ and $U_{a1}$), 1b (for measuring $I_1$ and $U_{b1}$), 2a (for measuring $I_2$ and $U_{a2}$), and 2b (for measuring $I_2$ and $U_{b2}$) are shown in FIGS. 18A, 18B, 18C, and 18D. A description of those elements of FIG. 17 that correspond to elements of FIG. 4, such as electrodes 304 to 304, switch 311, ports 311-1 to 311-4, AC source 320, ammeter 331, processor 350, contact impedance 361 to 364, bioimpedance 360, contact electrodes 371 to 374, and contact electrodes 381 to 384, is omitted.

FIGS. 18A, 18B, 18C, and 18D show current measurement paths for the embodiment of FIG. 17 according to various embodiments of the disclosure.

FIGS. 19, 20, 21, and 22 show other additional embodiments of a bioimpedance measurement device according to various embodiments of the disclosure.

Figure 19:
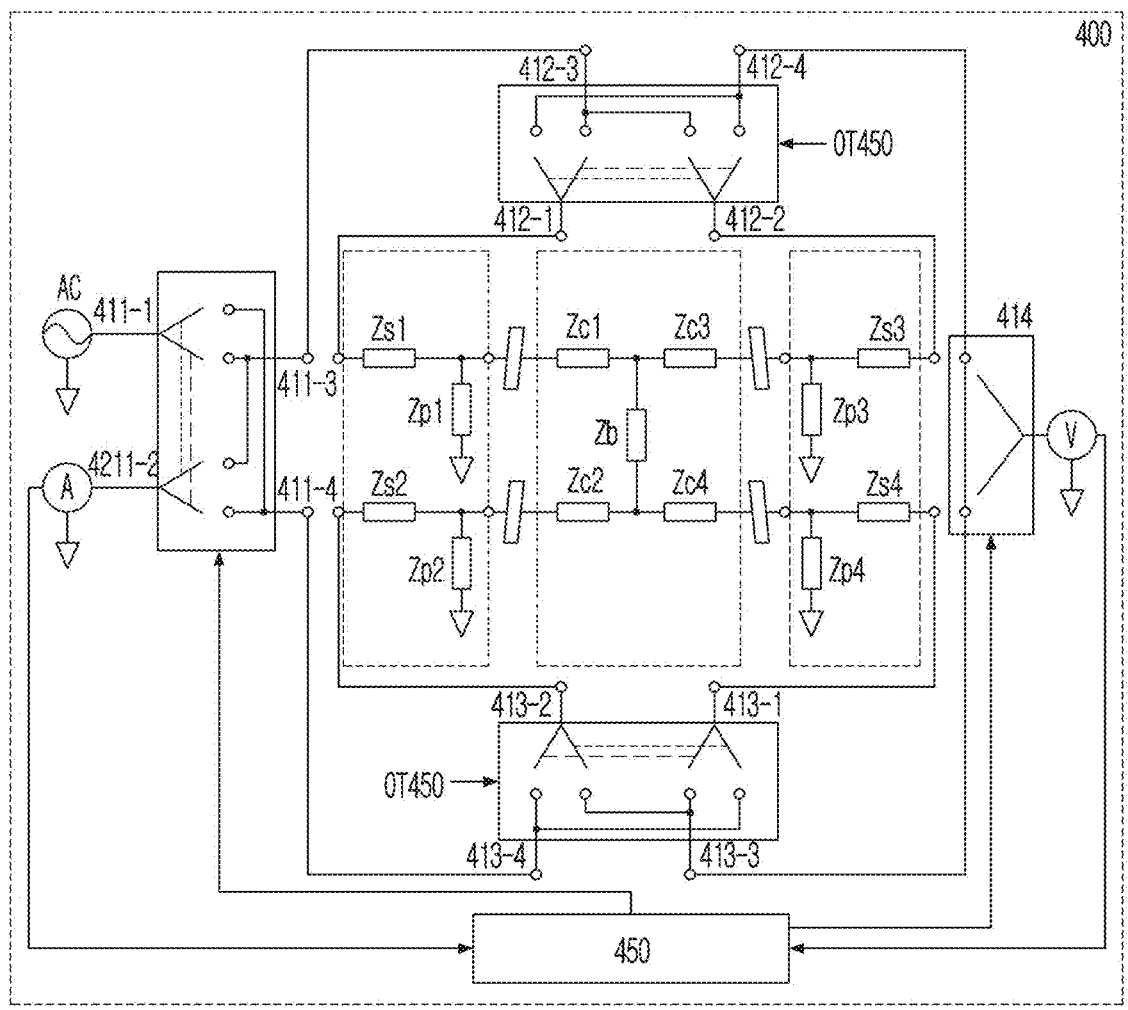
FIGS. 19, 20, 21, and 22 show other additional embodiments of a bioimpedance measurement device according to various embodiments of the disclosure.

FIG. 19 shows an embodiment of a bioimpedance measuring device 400 that is a combination of the previous two, in which, unlike the device 100 shown in FIG. 4, 3 additional switches are applied (412, 413, 414). The switches 412 and 413 may include corresponding ports 412-1 to 412-4 and 413-1 to 413-4. For each of 4 current measurement paths like those shown in FIGS. 16A to 16D, necessary is to measure the voltage with one voltmeter at two positions of switch 414, similarly as shown in FIGS. 18A to 18D. This structure has a higher accuracy than the device 300. A description of those elements of FIG. 19 that correspond to elements of FIG. 4, such as switch 411, ports 411-1 to 411-4, and processor 550, is omitted.

Figure 20:
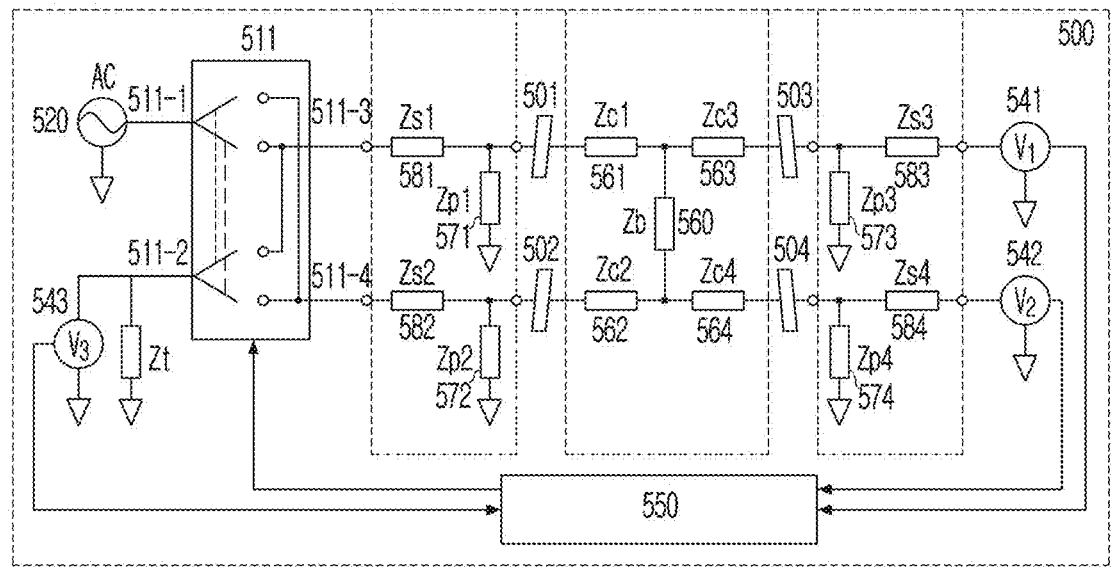

FIG. 20 illustrates an embodiment of a bioimpedance measuring device 500, wherein, unlike the device 100 shown in FIG. 4, instead of an ammeter, another current measurement circuit is used, for example, an additional voltmeter 543 (V3) measures the voltage drop (U) at a low impedance. The current in this case is $I=U/Z_r$. A description of those elements of FIG. 20 that correspond to elements of FIG. 4, such as electrodes 501 to 504, switch 511, ports 511-1 to 511-4, AC source 520, voltmeters 541 and 542, processor 550, contact impedance 561 to 564, bioimpedance 560, contact electrodes 571 to 574, and contact electrodes 581 to 584, is omitted.

Figure 21:
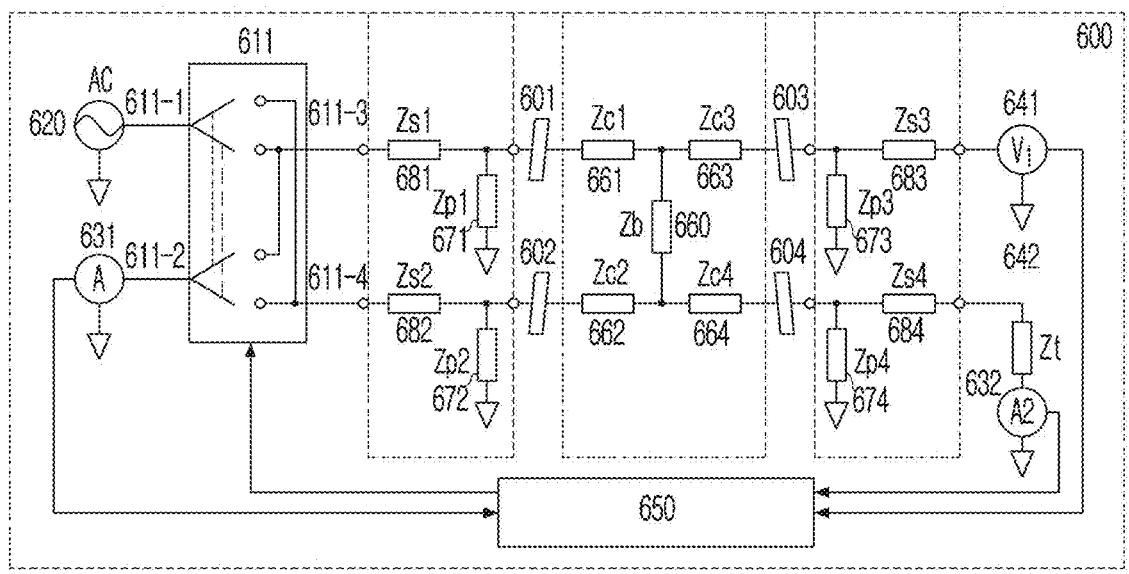

FIG. 21 shows an embodiment of a bioimpedance measuring device 600, wherein, unlike the device 100 shown in FIG. 4, instead of the first, the second or both voltmeters, another voltage measurement circuit is used, for example, instead of the second voltmeter (V2), an additional ammeter (A2) 632, which measures the current (1) in the corresponding branch with additional impedance $Z_r$. The voltage at the point before the impedance $Z_t$ in this case will be $U=1*Z_r$. A description of those elements of FIG. 21 that correspond to elements of FIG. 4, such as electrodes 601 to 604, switch 611, ports 611-1 to 611-4, AC source 620, ammeter 631, voltmeters 641 and 642, processor 650, contact impedance 661 to 664, bioimpedance 660, contact electrodes 671 to 674, and contact electrodes 681 to 684, is omitted.

Variants of the circuits were given above, wherein the peripheral components for each contact electrode are presented generally in the form of an equivalent circuit, in which there is one parallel parasitic impedance and one serial parasitic impedance. It should be understood that in fact, the peripheral components can be any other configuration of series and parallel connected elements.

Figure 22:
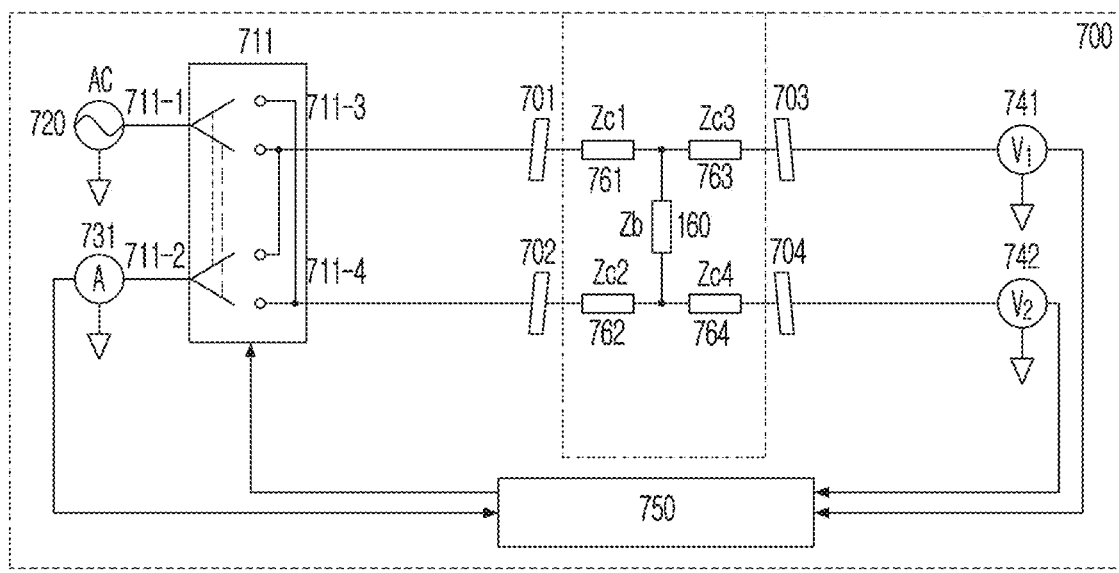

FIG. 22 shows an embodiment of a bioimpedance measuring device 700, wherein, unlike the device 100 shown in FIG. 4, peripheral components are absent or negligible (i.e. $Z_s$ and $1/Z_p$). Such variant, for example is possible, when the device is specifically intended for this function and does not have other functions, or when the peripheral components are well isolated from the bioimpedance measurement circuit. A description of those elements of FIG. 22 that correspond to elements of FIG. 4, such as electrodes 701 to 704, switch 711, ports 711-1 to 711-4, AC source 720, ammeter 731, voltmeters 741 and 742, processor 750, and contact impedance 761 to 764 is omitted.

In this document, an application scenario was described in which some contact electrodes touch wrist of one hand, and the user touches the other contact electrodes with fingers of the other hand Taking into account the versatility of the proposed device and method, it should be understood that in other embodiments a different scenario of use may be applied: for example, the user touches one pair of contact electrodes with the fingers of one hand, and touches the other pair with the fingers of the other hand. In other embodiments, it is possible to use contact electrodes intended for contact with the foot or other parts of the body. Knowing the range of typical contact impedances for the corresponding part of the body, which the contact electrode should touch, possible is to properly select the correction/weighting factors to obtain a highly accurate bioimpedance value.

In one embodiment, the device for bioimpedance determining may be, for example, a smart watch, and include a processor (control unit) that is configured to invoke and execute computer programs from memory to perform method steps or device unit functions in accordance with the embodiments of disclosure. According to the embodiments, the device may further include a memory. The processor can invoke and execute computer programs from the memory to perform the method for bioimpedance determining Memory can be a separate device independent of the processor, or can be integrated into the processor.

At least one of the steps in the method or the units in the device can use an artificial intelligence (AI) model to perform appropriate operations. The AI related function can be performed via nonvolatile memory, volatile memory and a processor.

The processor can include one or more processors. At the same time, one or more processors may be a general-purpose processor, such as a central processing unit (CPU), an application processor (AP), or the like, a graphics-only processing unit such as a graphics processing unit (GPU), a visual processor (VPU) and/or a specialized AI processor such as a neural processor (NPU).

One or more processors control the processing of input data in accordance with a predefined operation rule or an artificial intelligence (AI) model stored in nonvolatile memory and volatile memory. The predefined operation rule or the artificial intelligence model can be obtained through training. In this case, the processor can perform a preprocessing operation on the data to transform it into a form suitable for use as input to the artificial intelligence model.

"Obtained by way of training" means that by applying a training algorithm to a set of training data, the predefined operation rule or the AI model with a desired characteristic is created. The training can be performed on the device itself running the AI according to the embodiment, and/or can be implemented through a separate server/system.

The artificial intelligence model can include many layers of a neural network. Each of the plurality of layers of the neural network includes a plurality of weights and performs an operating operation for a given layer by calculating between the result of the calculation of the previous layer and the plurality of weights.

Examples of neural networks include, but are not limited to, Convolutional Neural Network (CNN), Deep Neural Network (DNN), Recurrent Neural Network (RNN), Restricted Boltzmann Machine (RBM), Deep Belief Network (DBN), Bidirectional Recurrent Deep Neural Network (BRDNN), generative adversarial networks (GANs), and deep Q-networks.

Training algorithm—is a method of training a predefined target device (such as a GPU-based neural network) using a variety of training data to invoke, enable, or control a target device to perform a determining or a prediction. Examples of training algorithms include, but not limited, supervised training, unsupervised training, part-time training, or reinforcement training.

Various illustrative units and modules described in connection with the disclosure herein may be implemented or executed by a general-purpose processor, digital signal processor (DSP), application specific integrated circuit (ASIC), field programmable gate array (FPGA), or other programmable logic device (PLD), discrete logic element or transistor logic, discrete hardware components, or any combination of the above, designed to perform the functions described herein. The general-purpose processor can be a microprocessor, but alternatively, the processor can be any conventional processor, controller, microcontroller, or a terminal machine. The processor can also be implemented as a combination of computing devices (for example, a combination of a DSP and a microprocessor, multiple microprocessors, one or more microprocessors with a DSP core, or any other similar configuration).

The abovementioned memory may be volatile or non-volatile memory, or may include both volatile and nonvolatile memory. Nonvolatile memory can be read only memory (ROM), programmable read only memory (PROM), erasable programmable read only memory (EPROM), electronic erasable programmable read only memory (EEPROM), or flash memory. Volatile memory can be random access memory (RAM). Also, the memory in embodiments of the disclosure may be static random access memory (SRAM), dynamic random access memory (DRAM), synchronous dynamic random access memory (synchronous DRAM, SDRAM), double bit rate synchronous dynamic random access memory, (SDRAM with double bit rate, DDR SDRAM), synchronous dynamic random access memory with enhanced speed (enhanced SDRAM, ESDRAM), DRAM with synchronous link DRAM (SLDRAM) and random access memory (DR RAM), etc. That is, memory in embodiments of the disclosure includes, but not limited to, these and any other suitable memory types.

The information and signals described herein can be represented using any of a variety of different technologies. For example, data, instructions, commands, information, signals, bits, symbols, and atomic signals, which may be exemplified in the above description, may be represented by voltages, currents, electromagnetic waves, magnetic fields or particles, optical fields or particles, or any combinations of the above.

The functions described in this document may be implemented in hardware, software executed by a processor, firmware, or any combination of the above. When implemented in software executed by a processor, the functions can be stored or transmitted as one or more instructions or code on a computer-readable medium. Other examples and implementations are within the scope of the disclosure of the disclosure. For example, due to the nature of software, the functions described above may be implemented using software executed by a processor, hardware, firmware, a fixed unit, or combinations of any of the above. Features that implement functions can also be physically located in different positions, including according to such a distribution that parts of the functions are implemented in different physical locations.

Computer-readable media includes both non-transitory computer storage media and communication media, including any transmission medium that facilitates movement of a computer program from one place to another. Non-transitory storage media can be any available media that can be accessed by a general purpose or special purpose computer. By way of example, and not limitation, non-transitory computer-readable media can include random access memory (RAM), read-only memory (ROM), electrically erasable programmable read-only memory (EEPROM), flash memory, compact disc (CD) or other optical disk storage device, magnetic disk storage device or other magnetic storage devices, or any other non-transitory medium that can be used to carry or store a desired program code means in the form of instructions or data structures, and which can be accessed by a general-purpose or special-purpose computer or a general-purpose or special-purpose processor.

It should be understood that this document shows the principle of operation and basic examples of a method and a device for bioimpedance determining A person skilled in the art using these principles will be able to obtain other embodiments of the disclosure without any creative effort.

Advantages of the Disclosure

Summarizing the above, it can be noted that the disclosure has the following advantages.
increasing the accuracy of determining a human body impedance;
simplification of both the construction and the method for bioimpedance determining;
using only one 2-position switch instead of a 4×4 switch matrix;
the need to carry out only 2 measurements;
no need for knowledge of preliminary data about the device (peripheral components, parasitic impedances, etc.);
reduction of required amount of memory;
reduction of energy consumption;
acceleration of measurement processing;
no need for additional calibration for each new model of devices;
no need to optimize algorithm for each new device model;
no need to collect new databases for each new device model;
reducing likelihood of human error in calibration and firmware;
no need to calculate the values of human contact impedances;
improving accuracy and ensuring correct use of the BIA for users with problem or diseased skin;
increasing accuracy and ensuring possibility of correct measurement under any condition of the skin of any individual user (normal, wet, dry, damaged);
increasing accuracy and ensuring possibility of correct measurement at any force of contact of the skin with the contact electrode;
increasing accuracy and ensuring possibility of correct measurement in any state of the environment (high or low humidity, temperature);
improved user experience;
ensuring possibility of reducing the contact electrode size and increasing compactness of the device;
weak dependence on the signal generator frequency and ensuring possibility of using multifrequency BIA;
reduction of costs and time for the device production;
reducing requirements for the component base;
ensuring possibility of using various designs and materials of the device.

A person skilled in the art should understand that not each of the above advantages is necessarily inherent in every single embodiment, that is, different embodiments may have a different set of the listed advantages and to different extent.

APPLICATION

The devices and methods for bioimpedance determining according to the disclosure can be used in electronic devices, wherein required is to determine body constitution (percentage of lean mass, fat mass, water, muscle mass, bone tissue, body mass index, metabolic rate, biological age, predisposition to those or other diseases, etc.). The disclosure is suitable for any form-factor, including: for compact wearable devices such as electronic bracelets, smart watches, for mobile devices such as smartphones, tablets, for household appliances such as refrigerators, scales, for medical equipment etc.

It should be understood that although terms such as "first," "second," "third" and the like may be used herein to describe various elements, components, regions, layers and/or sections, these elements, components, regions, layers and/or sections should not be limited by these terms. These terms are used only to distinguish one element, component, region, layer or section from another element, component, region, layer or section. Thus, a first element, component, region, layer, or section may be called a second element, component, region, layer or section without departing from the scope of the disclosure. As used herein, the term "and/or" includes any and all combinations of one or more of the respective listed positions. Elements mentioned in the singular do not exclude the plurality of elements, unless otherwise specified.

Functionality of an item referred to in the specification or claims as a single item may be practiced by several device components, and vice versa, functionality of items specified in the description or claims as several separate items can be implemented in practice by a single component.

In one embodiment, the elements/units of the proposed device are located in a common housing, can be placed on the same frame/structure/printed circuit board and are structurally connected to each other by means of mounting (assembling) operations and functionally by means of communication lines. Mentioned communication lines or channels, unless otherwise indicated, are standard communication lines known to those skilled in the art, the material implementation of which does not require creative efforts. The communication line can be a wire, a set of wires, a bus, a track, a wireless communication line (inductive, radio frequency, infrared, ultrasonic, etc.). Communication protocols over communication lines are known to specialists and are not disclosed separately.

Functional connection of elements should be understood as a connection that ensures correct interaction of these elements with each other and implementation of one or another functionality of the elements. Particular examples of functional communication can be communication with the ability to exchange information, communication with the ability to transmit electric current, communication with the ability to transmit mechanical movement, communication with the ability to transmit light, sound, electromagnetic or mechanical vibrations, etc. A specific type of functional connection is determined by the nature of the interaction of these elements, and, unless otherwise specified, is provided by widely known means using principles widely known in the prior art.

Electrical connection of one element/circuit/port/output to another element/circuit/port/output implies that these elements/circuits/ports/outputs can be either directly connected to each other or indirectly through other elements or circuits.

Design implementation of the elements of the proposed device is known to specialists in this field of technology and is not described separately in this document, unless otherwise indicated. The elements of the device can be made of any suitable material. These constituent parts can be manufactured using known methods, including, by way of example only, machining, investment casting, crystal growth. Operation of assembling, connecting and other operations in accordance with the above description also correspond to the knowledge of a person skilled in the art and, therefore, will not be explained in more detail here.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A device for determining bioimpedance, the device comprising:
   first and third contact electrodes, configured to contact a first part of a user's body;
   second and fourth contact electrodes configured to contact a second part of the user's body, the first part being different from the second part;
   an alternating current source;
   a current measurement circuit, wherein the alternating current source and the current measurement circuit have a common ground;
   at least one voltage measurement circuit configured to measure a voltage between one of the first and third contact electrodes and the common ground, and between one of the second and fourth contact electrodes and the common ground;
   a first switch comprising four ports, a first port being connected to the alternating current source, a second port being connected to the current measurement circuit, the first switch having at least two states and configured to form, in a first state and a second state, respectively, first and second current measuring paths so that a current flows through the user's body from the first part of the user's body to the second part of the user's body; and
   a control unit connected to the first switch, to the current measurement circuit and to the at least one voltage measurement circuit, and configured to:
      control the states of the first switch,
      receive current and voltage values measured by the current measurement circuit and the at least one voltage measurement circuit for each current measurement path, and
      determine a bioimpedance of the user based on the received current and voltage values.

2. The device of claim 1,
   wherein, when the first switch is configured in the first state, the first and the second ports are connected, respectively, with third and fourth ports, and
   wherein, when the first switch is configured in the second state, the first and the second ports are connected, respectively, with the fourth and the third ports.

3. The device of claim 1,
   wherein a third port of the first switch is electrically connected with the first contact electrode, and
   wherein a fourth port of the first switch is electrically connected with the second contact electrode.

4. The device of claim 1, wherein the voltage measurement circuit is an ammeter with an impedance connected in series thereto or a voltmeter.

5. The device of claim 1, wherein the current measurement circuit is a voltmeter with an impedance connected in parallel thereto or an ammeter.

6. The device of claim 1,
   wherein the at least one voltage measurement circuit includes a first voltage measurement circuit and a second voltage measurement circuit,
   wherein the first voltage measurement circuit is electrically connected with the third contact electrode and the common ground, and
   wherein the second voltage measurement circuit is electrically connected with the fourth contact electrode and the common ground.

7. The device of claim 1,
   wherein a number of the voltage measurement circuits is one, and
   wherein the device further comprises a fourth switch configured to alternately connect each of the third and the fourth contact electrodes with the voltage measurement circuit for each of the current measurement paths.

8. The device of claim 1, further comprising:
   a second and a third switch, each of which comprises four ports and is connected with the control unit,
   wherein a third port of the first switch is connected with a third port of the second switch,
   wherein a fourth port of the first switch is connected with a fourth port of the third switch,
   wherein a first port of the second switch is electrically connected with the first contact electrode,
   wherein a second port of the second switch is electrically connected with the third contact electrode,
   wherein a first port of the third switch is electrically connected with the fourth contact electrode,
   wherein a second port of the third switch is electrically connected with the second contact electrode,
   wherein a fourth port of the second switch and a third port of the third switch are configured to connect to the at least one voltage measurement circuit, and
   wherein the first switch, the second switch, and the third switch have at least two states and are configured to jointly form at least four different current measurement paths so that the current flows through the user's body from one body part to another body part.

9. The device of claim 8,
   wherein the at least one voltage measurement circuit includes a first voltage measurement circuit and a second voltage measurement circuit,
   wherein the first voltage measurement circuit is connected to the fourth port of the second switch and the common ground, and
   wherein the second voltage measurement circuit is connected to the third port of the third switch and the common ground.

10. The device of claim 8,
   wherein a number of the voltage measurement circuits is one, and wherein the device further comprises a fourth switch configured to alternately connect each of the fourth port of the second switch and the third port of the third switch to the voltage measurement circuit for each of the current measurement paths.

11. The device of claim 1, further comprising:
at least one additional element and/or circuit, which cause serial and/or parallel parasitic impedance in the circuit between a corresponding contact electrode and a corresponding switch port, and/or in the circuit between a corresponding contact electrode and a corresponding output of the voltage measurement circuit.

12. A method for determining bioimpedance, performed in a device for determining bioimpedance the method comprising:
controlling a first switch to change a state of the first switch to a first state or a second state for forming, respectively, a first or a second current measurement paths, the first current measurement path being formed when the first switch is in the first state in which a current flows through a user's body through a first contact electrode contacting a first part of the user's body to a second contact electrode contacting a second part of the user's body, and the second current measurement path being formed when the first switch is in the second state and a current flows through the user's body in the opposite direction through the second contact to the first contact;
in each of the current measurement paths, measuring the current ($I_1$, $I_2$) in a region of one contact electrode, to which the current flows through the user's body;
in each of the current measurement paths, measuring a voltage ($U_{a1}$, $U_{a2}$) in a region of another contact electrode contacting the first part of the user's body and a ground, and a voltage (Uht, Ubz) between another contact electrode contacting the second part of the user's body and the ground; and
determining a bioimpedance ($Z_b$) of the user based on the measured current and voltage values.

13. The method of claim 12, wherein the bioimpedance of the user is determined according to the following formula:

$$Z_b = \frac{\frac{U_{a1}}{U_{b1}} - \frac{U_{b1}}{U_{a1}} + \frac{U_{a2}}{U_{b2}} - \frac{U_{b2}}{U_{a2}}}{I_1\left(\frac{1}{U_{a1}} + \frac{1}{U_{b1}}\right) + I_2\left(\frac{1}{U_{a2}} + \frac{1}{U_{b2}}\right)}.$$

14. The method of claim 12, further comprising:
determining a corrected bioimpedance ($Z_{bcorr}$) of the user based on the determined bioimpedance ($Z_b$) of the user by using a pretrained neural network.

15. The method of claim 14, further comprising:
pretraining the neural network with a method of linear regression by applying a training model directed to minimizing an error between reference values of bioimpedance ($Z_{bref}$) from a training sample, measured for each user on a reference equipment, and bioimpedance ($Z_b$) values, determined for each user from the training sample, without correction.

16. The method of claim 15, wherein the training model further considers at least one of the following parameters for each user from the training sample:
weight, height, age, gender, race, waist circumference, hip circumference, or wrist circumference.

17. The method of claim 12,
wherein the device for bioimpedance measuring further comprises:
second and third switches, each having at least two states, and wherein the method further comprises:
controlling a state of the first switch, a state of the second switch, and a state of the third switch to form four different current measurement paths, wherein the current flows through the user's body through one of the contact electrodes contacting the first part of the user's body to one of the contact electrodes contacting the second part of the user's body,
measuring the current ($I_1$, $I_2$, $I_3$, $I_4$) in each of the current measuring paths in the region of the one contact electrode to which the current flows through the user's body,
measuring the voltage ($U_{a1}$, $U_{a2}$, $U_{a3}$, $U_{a4}$) in each of the current measuring paths between one of the contact electrodes contacting the first part of the user's body and the ground, and the voltage ($U_{b1}$, $U_{b2}$, $U_{b3}$, $U_{b4}$) between one of the contact electrodes contacting the second part of the user's body and the ground, and
determining bioimpedance ($Z_b$) of the user based on the measured current and voltage values according to the following formula:

$$Z_b = \frac{\frac{U_{a1}}{U_{b1}} - \frac{U_{b1}}{U_{a1}} + \frac{U_{a2}}{U_{b2}} - \frac{U_{b2}}{U_{a2}} + \frac{U_{a3}}{U_{b3}} - \frac{U_{b3}}{U_{a3}} + \frac{U_{a4}}{U_{b4}} - \frac{U_{b4}}{U_{a4}}}{I_1\left(\frac{1}{U_{a1}} + \frac{1}{U_{b1}}\right) + I_2\left(\frac{1}{U_{a2}} + \frac{1}{U_{b2}}\right) + I_3\left(\frac{1}{U_{a3}} + \frac{1}{U_{b3}}\right) + I_4\left(\frac{1}{U_{a4}} + \frac{1}{U_{b4}}\right)}.$$

18. The method of claim 12, further comprising:
compensating for parasitic impedance present in the current measurement paths.

19. The method of claim 12, further comprising:
compensating for impedance caused by other components of the device for determining bioimpedance.

20. The method of claim 12,
wherein the first state is a state in which the current flows through the first current measurement path, and
wherein the second state is a state in which the current flows through the second current measurement path.

* * * * *